United States Patent
Mutch et al.

[11] Patent Number: 5,941,841
[45] Date of Patent: Aug. 24, 1999

[54] CONTROL OF LIFE SUPPORT SYSTEMS

[75] Inventors: William Alan C. Mutch; Gerald Robin Lefevre, both of Winnipeg, Canada

[73] Assignee: University of Manitoba, Winnipeg, Canada

[21] Appl. No.: 08/834,205

[22] Filed: Apr. 15, 1997

Related U.S. Application Data

[63] Continuation of application No. 08/404,464, Mar. 15, 1995, Pat. No. 5,647,350.

[30] Foreign Application Priority Data

Mar. 15, 1994 [GB] United Kingdom .................... 9405002

[51] Int. Cl.$^6$ ..................................................... A61M 37/00
[52] U.S. Cl. ..................................................................... 604/4
[58] Field of Search .......................... 604/4–6, 34; 251/4, 251/5

[56] References Cited

U.S. PATENT DOCUMENTS

| | | | |
|---|---|---|---|
| 4,448,192 | 5/1984 | Stawitcke et al. | 128/204.26 |
| 5,129,390 | 7/1992 | Chopin et al. | 128/204.21 |
| 5,186,431 | 2/1993 | Tamari | 604/4 |
| 5,316,009 | 5/1994 | Yamada | 128/716 |

FOREIGN PATENT DOCUMENTS

| | | |
|---|---|---|
| 2 624 744 | 6/1989 | France . |
| 2 025 662 | 1/1980 | United Kingdom . |
| WO 93/10844 | 6/1993 | United Kingdom . |

OTHER PUBLICATIONS

Suki et al. (Nature, vol. 368, Apr. 1994, pp. 615–618).

Croughwell et al. (Ann. Thorac. Surg. 1994, 58:1702–1708).

Maeda, K. et al., Asaio Transactions, "Predictive Control by Physical Activity Rate of a Total Artificial Heart During Exercis", vol. 34, No. 3, Jul. 1988, 480–484.

Michael Heymann et al., "Blood Flow Measurements with Radionuclide–labeled Particles", Progress in Cardiovascular Diseases, vol. XX, No. 1 (Jul./Aug.), 1977, pp. 55–79.

*Primary Examiner*—John G. Weiss
*Assistant Examiner*—Ki Yong O
*Attorney, Agent, or Firm*—Sim & McBurney

[57] ABSTRACT

The flow of a biological fluid to an organ is computer-controlled so that the natural variation of such flow is simulated. Specifically described are control of a blood pump flow output during CPB to mimic normal pulsatile blood flow from the heart and control of a ventilator output to mimic normal breathing of healthy lungs. A pattern of variation over time of instantaneous flow of a biological fluid to an organ of a mammalian species is established, a variable control parameter for regulation of flow of the biological fluid to the organ is generated in accordance with the pattern, and the flow of biological fluid to the organ is controlled in accordance with the variable control parameter.

2 Claims, 39 Drawing Sheets

CONTROL OF LIFE SUPPORT SYSTEMS

This is a continuation of application Ser. No. 08/404,464 filed Mar. 15, 1995 now U.S. Pat. No. 5,647,350.

FIELD OF INVENTION

The present invention relates to medical life support systems, and, in particular, to the control of cardiopulmonary bypass pumps for open heart surgery and mechanical ventilators to lungs.

BACKGROUND TO THE INVENTION

During cardiopulmonary bypass surgery (CPB), the most common operation conducted in North America, the heart is stopped and the blood which normally returns to the right side of the heart passes through a pump and oxygenating system and is returned to the aorta, thereby bypassing the heart and lungs. The flow of blood is essentially non-pulsatile with a low amplitude waveform having monotonous regularity.

Although a common procedure (in excess of 400,000 open heart procedures per annum are conducted in North America) and although tremendous strides have been made so that open heart surgery is safer for patients, the procedure is not without its dangers. Although the vast majority of patients have marked improvement in their cardiac functional status following their procedure, of concern is the potential for damage to other organ systems which can occur due to the need for CPB.

The following consequences have been identified with conventional non-pulsatile CPB, namely metabolic acidosis, interstitial fluid accumulation, elevated systemic vascular resistance, arteriovenous shunting and impaired brain oxygenation. Of greatest concern is the potential for neurologic damage. Increasingly, well conducted prospective trials have demonstrated an alarming rate of post-operative neuropsychologic disturbances following cardiac surgery. Recent studies have shown that up to 60 percent of patients undergoing open heart surgery have neuropsychologic deficits following their operation, so that as many as 240,000 patients per annum may develop neurologic abnormalities following cardiac surgery. These disturbances are subtle but involve higher cognitive functions of the brain.

Mechanical ventilation of the lungs represents one of the major accomplishments of modern medicine and is one of the cornerstones upon which modern surgery and intensive care is based. Despite many major advances, mechanical ventilation is still associated with a number of alterations in respiratory function which causes morbidity and mortality in patients requiring this type of support. Inability to maintain gas exchange remains one of the major limiting factors with regard to life-support of critically ill patients. Even in healthy patients being ventilated during elective surgery, alterations in gas exchange can be demonstrated. These relate to collapse of small airways and alveoli. Prevention of these alterations would likely represent a major advance in management of all patients requiring ventilatory support. Conventional mechanical ventilation is monotonously regular in delivery of set tidal volume and respiratory rate.

The monotonous regularity of pumping of blood during CPB and of set tidal volume and respiratory rate of a mechanical ventilator is in contrast to the intrinsic spontaneously variable rhythms of heart rate, blood pressure and respiration, associated with a normal functioning heart as well as the considerable range of tidal volume and respiratory rate which a healthy individual demonstrates during breathing.

SUMMARY OF THE INVENTION

In the present invention, the operation of a blood pump and mechanical ventilator are controlled to provide a flow of blood on the one hand and medical gases on the other which is varied in a manner that closely mimics the natural variation action of the heart and lungs and thereby overcomes some of the defects noted above. The invention is not applicable only to these two devices but is applicable to regulation in control of flow of any biological fluid to any organ. Although the existence of such variability in biological fluid flow is known, no one has heretofore taken such variability into account during the application of life support systems.

Blood is pumped in a monotonously regular non-pulsatile fashion or low amplitude pulsatile manner.

In the present invention, a pattern of variations over time of instantaneous changes in flow of a biological fluid to an organ of a mammalian species first is generated. The mammalian species may be the human to whom the procedure is to be applied, another human or another mammalian species which is a model for a human, such as, a dog or a pig. The generated pattern may be an actual pattern determined from the mammalian species or may be a computer simulation of the known variation in the flow. The generated pattern generally is provided with a sufficient number of determinations as to be representative of normal variation. Depending on the procedure involved, the pattern of variation may be established for the appropriate change in flow. For example, for control of blood pump during CPB, a pattern of variation over time of instantaneous blood pressure and heart rate is established. For control of a ventilator device, a pattern of variation over time of instantaneous respiratory rate and tidal volume is established.

A variable control parameter then is generated for regulation of flow of the biological fluid to an organ in accordance with the pattern. This control parameter is most readily achieved by computer processing of the pattern of variation. In effecting such computer processing, the individual values of the parameter in the pattern and the peak-to-peak time interval between the individual values are recorded and analyzed. For example, for control of a CPB pump, each of the individual blood pressures for the pattern of instantaneous blood pressure and heart rate and the time interval (heart rate) between each of the individual blood pressures are recorded. For control of a ventilator, each of the individual respiratory rates and tidal volumes for the pattern of instantaneous respiratory rate and tidal volumes and the time interval between each of the individual respiratory rates and. tidal volumes are recorded.

The variable control parameter generated in the procedure of the invention depends on the flow of biological fluid being regulated. In the case of the CPB pump, a signal is generated corresponding in value to an individually-determined blood pressure for a period of time corresponding to the heart rate for the difference between the one individually-determined blood pressure and the next individually-determined blood pressure of the pattern. In the case of the ventilator, a signal is generated corresponding in value to an individually-determined respiratory rate and tidal volume.

In the present invention, the next step is to control the flow of biological fluid to the organ in accordance with the variable control parameter. In this way, the flow of biological fluid to the organ is effected in accordance with the pre-established pattern of variation over time and hence mimics the natural flow of the biological fluid to the organ.

The manner of control of the flow of biological fluid to the organ depends on the biological fluid and the organ concerned. For example, in the case of the control of a CPB pump, a control voltage is generated corresponding in magnitude to the generated signal from the variation pattern and the control voltage is applied to the pump to provide an output of blood from the pump of a pressure proportional to the magnitude of the signal for the period of time (peak-to-peak time interval). The steps of generating a signal, generating a control voltage and applying the control voltage to the pump then is repeated for each next individually-determined blood pressure of the pattern. Depending on the duration of the operation and the number of individual determinations in the pattern, it may be necessary to repeat these steps again for the pattern, reading either from the beginning or in the reverse direction. In this way, a pulsatile flow of blood from the pump is provided to the CPB patient which mimics normal pulsatile blood flow from the heart.

Similarly, for the control of ventilating gas from a ventilator, a control voltage is generated corresponding in magnitude to the generated signal from the variable pattern and the control voltage is applied to the ventilator device to provide an output of ventilating gas from the ventilator device of a respiratory rate proportional to the magnitude of the signal. The steps of generating a signal, generating a control voltage and applying the control voltage to the ventilation device are repeated for each next individually-determined respiratory rate of the pattern. In this way, a variable flow of ventilating gas from the ventilator device is provided which mimics normal breathing of healthy lungs.

As noted above, the present invention is applicable not only to control of a CPB pump or a mechanical ventilator but also to any other operation or device involving this control of a biological fluid to any organ. For example, the principles of the invention may be used in intra aortic balloon counterpulsation (IABC), the technique used to support patients, usually following CPB, when they are unable to maintain adequate cardiac output, until enough heart function has returned to permit its discontinuation.

The principles of the invention may be employed to improve hemodialysis by introducing variability to the pumping to provide improved diffusion across the dialysis membrane by promoting better mixing of blood and avoidance of areas of relatively stagnant flow and thereby decreasing dialysis time.

In addition, the present invention may be employed with extracorporeal membrane oxygenation (ECMO), which is a modification of CPB in which bypass is instituted to support the patient while giving the lungs a chance to heal. The patient is ventilated while on ECMO and if the therapy is successful, eventually weaned off ECMO and the ventilator. Computer control of the CPB pump in this situation has the potential to enhance organ perfusion, while computer-controlled ventilation has the potential to activate lung healing and of improving gas exchange in order to facilitate earlier weaning from ECMO.

The present invention further may be employed in conjuction with right and left ventricular assist devices (RVAD and LVAD), which are occasionally used to support patients after CPB when they are unable to maintain adequate output without this type of support. Patients given such support are simultaneously being ventilated. Computer-controlled ventilation and computer-controlled RVAD and LVAD, as provided herein, may improve organ perfusion while computer-controlled ventilation may indirectly influence hemodynamic variability.

Another application of the principles of the present invention is in the perfusion of organs prior to transplantation.

BRIEF DESCRIPTION OF DRAWINGS

Referring to FIG. 14, the wiper of the 'VOLUME' control is buffered by aplifier U1D, and coupled to a non-inverting summing amplifier (U1C), whose output is routed back to the 'VOLUME' control's original destination (label 'VOL CTRL' is connected to FIG. 13 amplifier U5D). The 'VOLUME' output at U1D is also routed to the A/D converter channel 0 input (U2A), and the 'VOL POT MONITOR' (U2B), which allows optional monitoring of the Ohio 7000's 'VOLUME' control level before modulation is inserted (J1 on FIG. 2). The modulation reference signal from the D/A converter channel 0 output is buffered and scaled (I1A and U1B) and routed to the other input of the non-inverting summing amplifier (U1C), whose output is also routed to A/D converter channel 1 input (U2C), and to U2D —the 'VOL MONITOR' (J2 on FIG. 12), which allow optional monitoring of 'VOLUME' after modulation is inserted. Since the D/A converter's output is in a range between 0 and 5 volts, the modulation level only increases the 'VOLUME', hence the position of the ventilator's 'VOLUME' control sets the minimum or baseline level of 'VOLUME'.

DESCRIPTION OF PREFERRED EMBODIMENT

Figure 1:
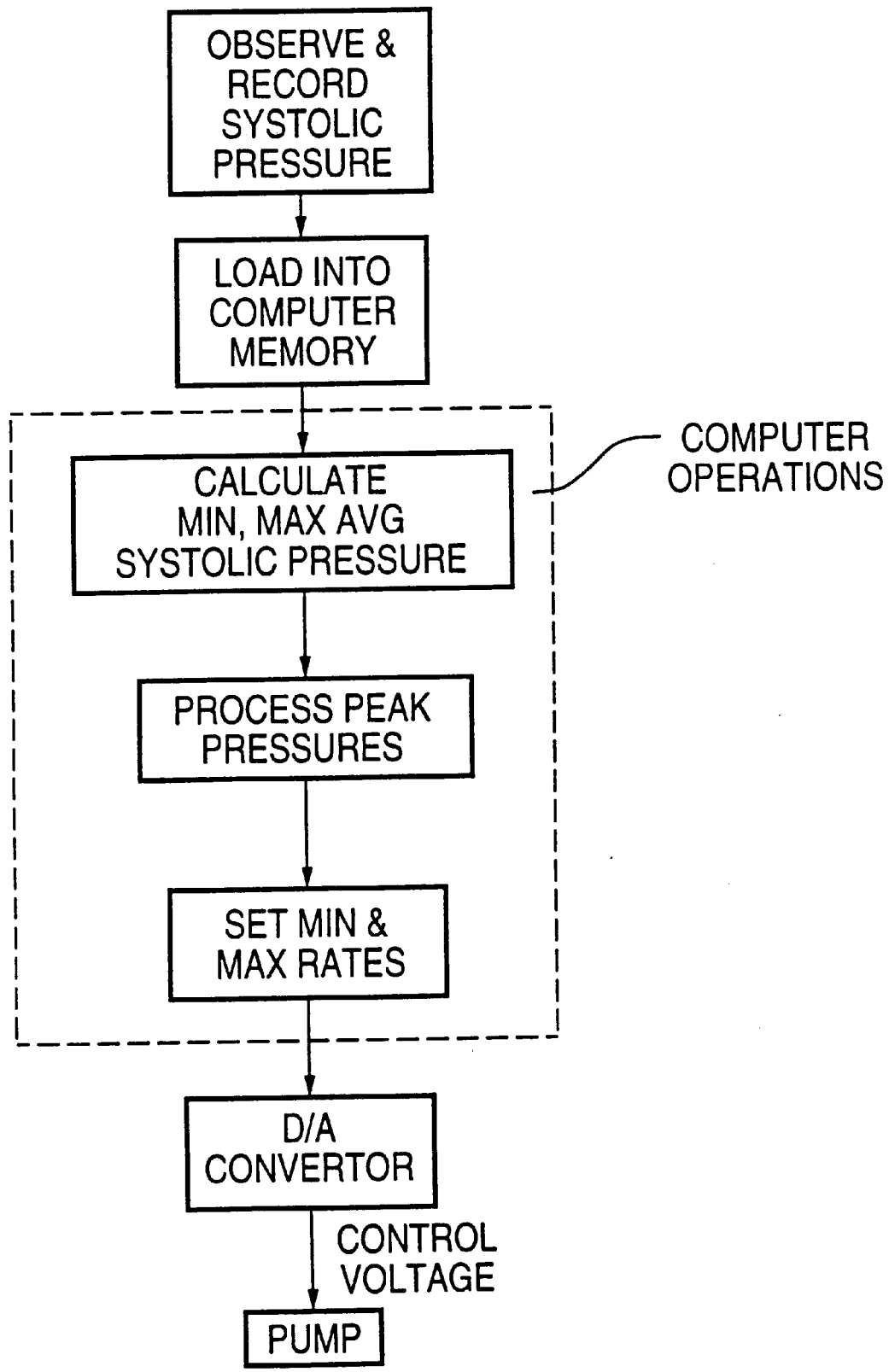
FIG. 1 is a flow diagram showing the various steps of the operation of a CPB pump in accordance with one embodiment of the invention.

In the following description of a preferred embodiment, there is description of the application of the present invention to control of a blood pump. However, it will be understood that the principles described with respect to such blood pump embodiment apply to other devices, including control of ventilators as described elsewhere. The steps involved are shown schematically in FIG. 1.

During a CPB procedure, an electrically-driven pump is used to maintain blood flow, as described above. Generally, a roller pump is employed for this function, in which a pair of diametrically opposed rotating arms engage a flexible tube through which blood is forced by the action of the arms engaging the flexible tube.

Figure 2:
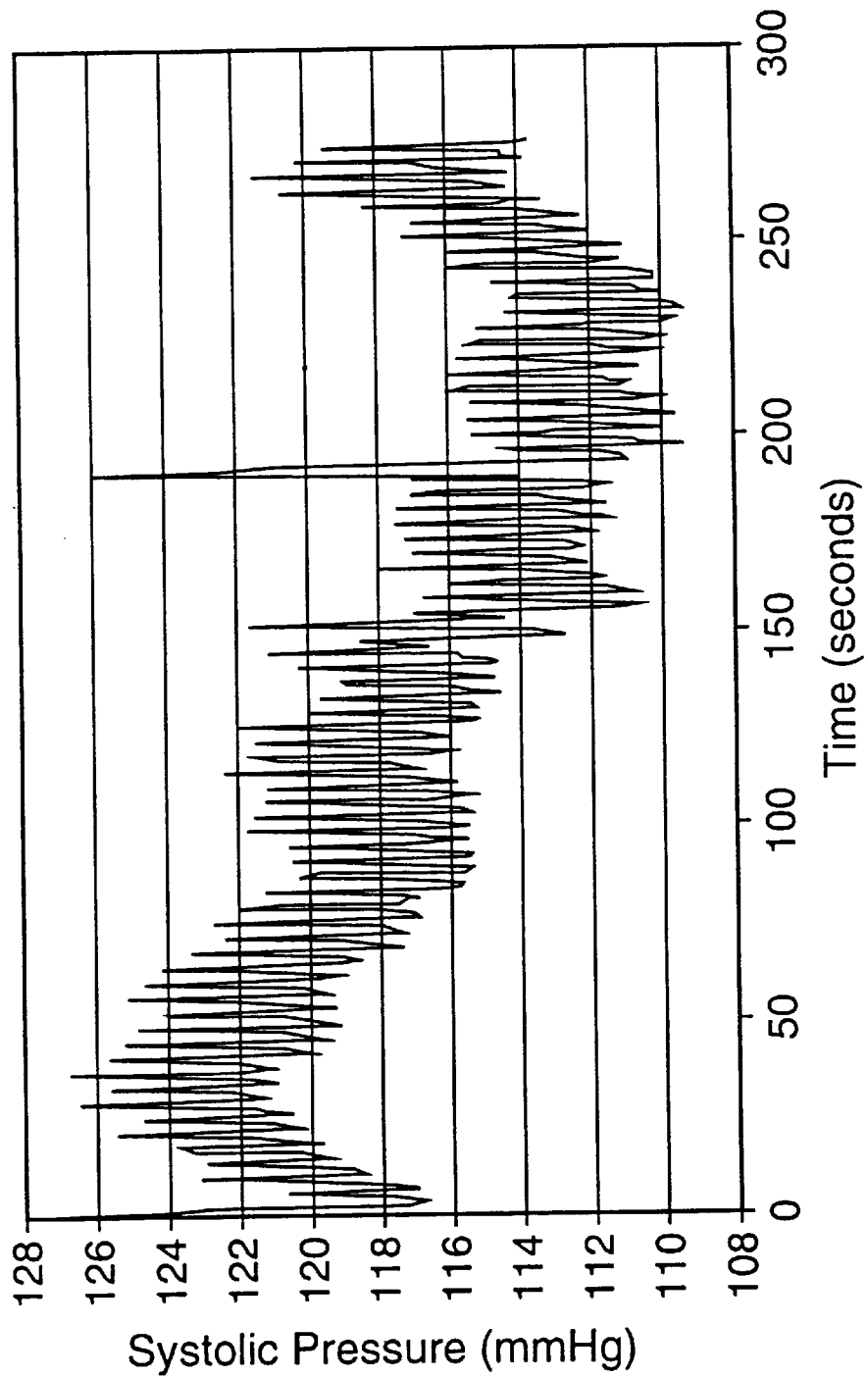
FIG. 2 shows a typical plot of natural variation of systolic blood pressure over time. In this instance, in a dog, data is captured to a data acquisition system from a dog. Following processing, these data are used as an input file for the computer controller used to vary roller pump head revolutions/min based on variability in beat-to-beat intervals and pressure.

An input file for a computer-controller for the pump first is established for the variation of systolic pressure with time for a typical animal, such as a human, a dog or a pig. A typical plot of the gross variation of systolic pressure in mm Hg over time is shown in FIG. 2.

This information, which may contain many thousands of observations of systolic pressure, is loaded into the computer memory and processed by peak height analysis. In this peak height analysis, the maximum, minimum average systolic pressures are determined and may be displayed, the minimum values are removed and the minimum, maximum and average of the remaining peak pressures is recalculated and, if desired, displayed. This information then determines the pulse pressure amplitude and beat-to-beat heart beat variation in the pattern.

Figure 3:
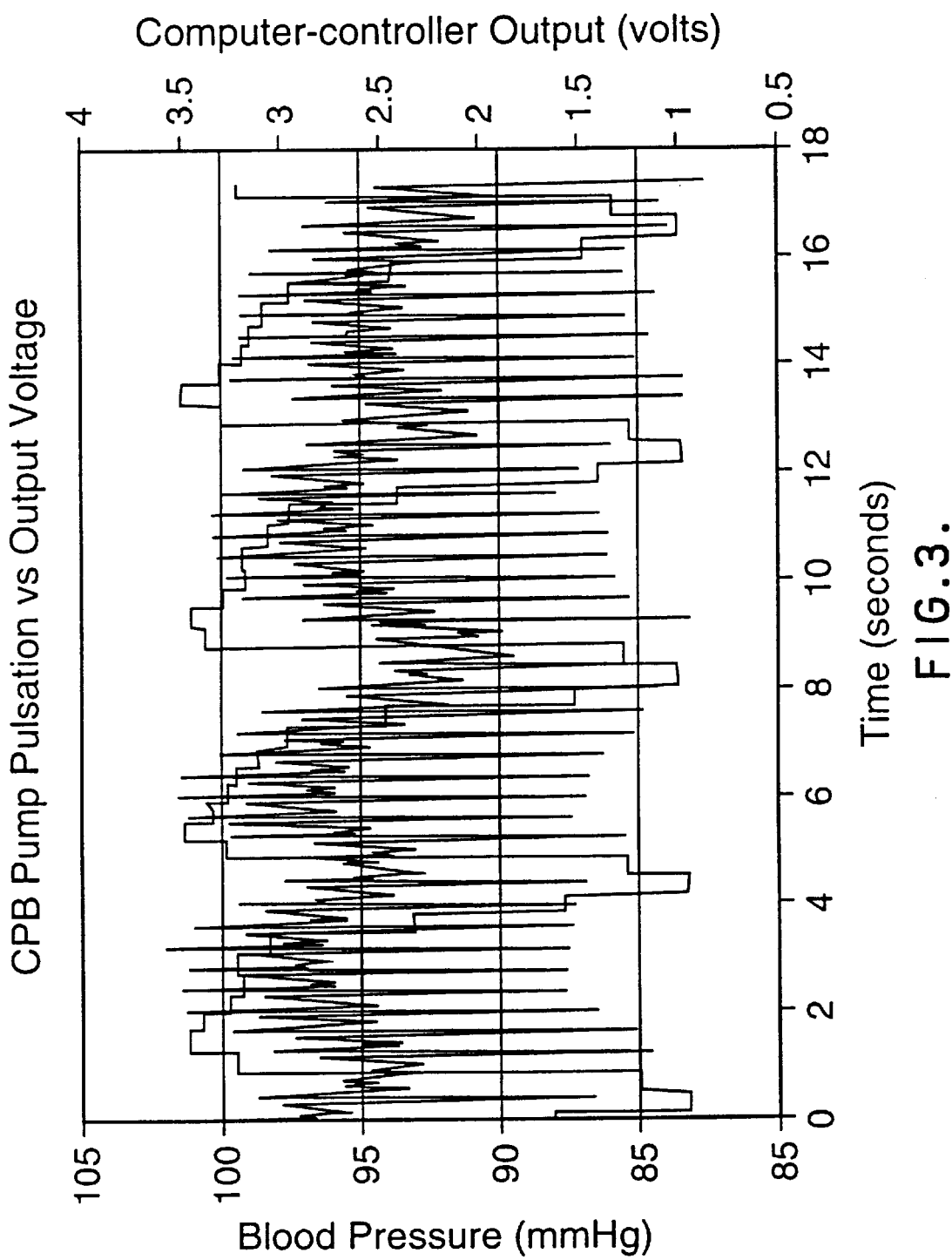
FIG. 3 shows a typical pump pulsation profile for a blood pump controlled in accordance with the invention superimposed upon a plot of peak-to-peak variations in blood pressure derived from a plot similar to that shown in FIG. 2.

The lowest and highest values of the pressure values from the peak-to-peak variation then are established and these values are used to set a minimum and maximum rate for the blood pump, respectively, which then determines the maximum amount of computer modulation. For example, a baseline pressure of 80 mm Hg with a 20 mm Hg variation may be established based on the input file, which then provides a peak pressure ranging from 80 to 100 mm Hg. The computer digital output signal corresponding in magnitude to a peak-to-peak value above the minimum is connected through a digital-to-analog (D/A) converter, which produces an analog voltage control signal to the blood pump to increase the blood pump rate. The computer generates a voltage on the D/A converter proportional to the peak pressure variations for a time proportional to the beat-to-beat interval. The voltage then is used to increase the rpm of the pump from the minimum or baseline setting. The data stored in memory is converted into time steps and relative amplitudes from 0 to 100%. For each time step, the D/A drive is held at the relative level until the next time step occurs. A typical pump pulsation profile superimposed upon a plot of peak-to-peak variations in blood pressure is shown in FIG. 3. As may be seen in FIG. 3, over a period of approximately 18 seconds, the computer-controller output varies between 1 and 3.5 volts. The changes in roller pump speed has resulted in escalations in blood pressure varying between 82 and 102 mm Hg. The data stored in memory is initially scanned in a forward direction for observations 1 to N. As necessary, the data is reverse scanned continuously from observations N-1 to 1 and then forwards from 2 to N. etc. until the program is terminated.

Figure 4:
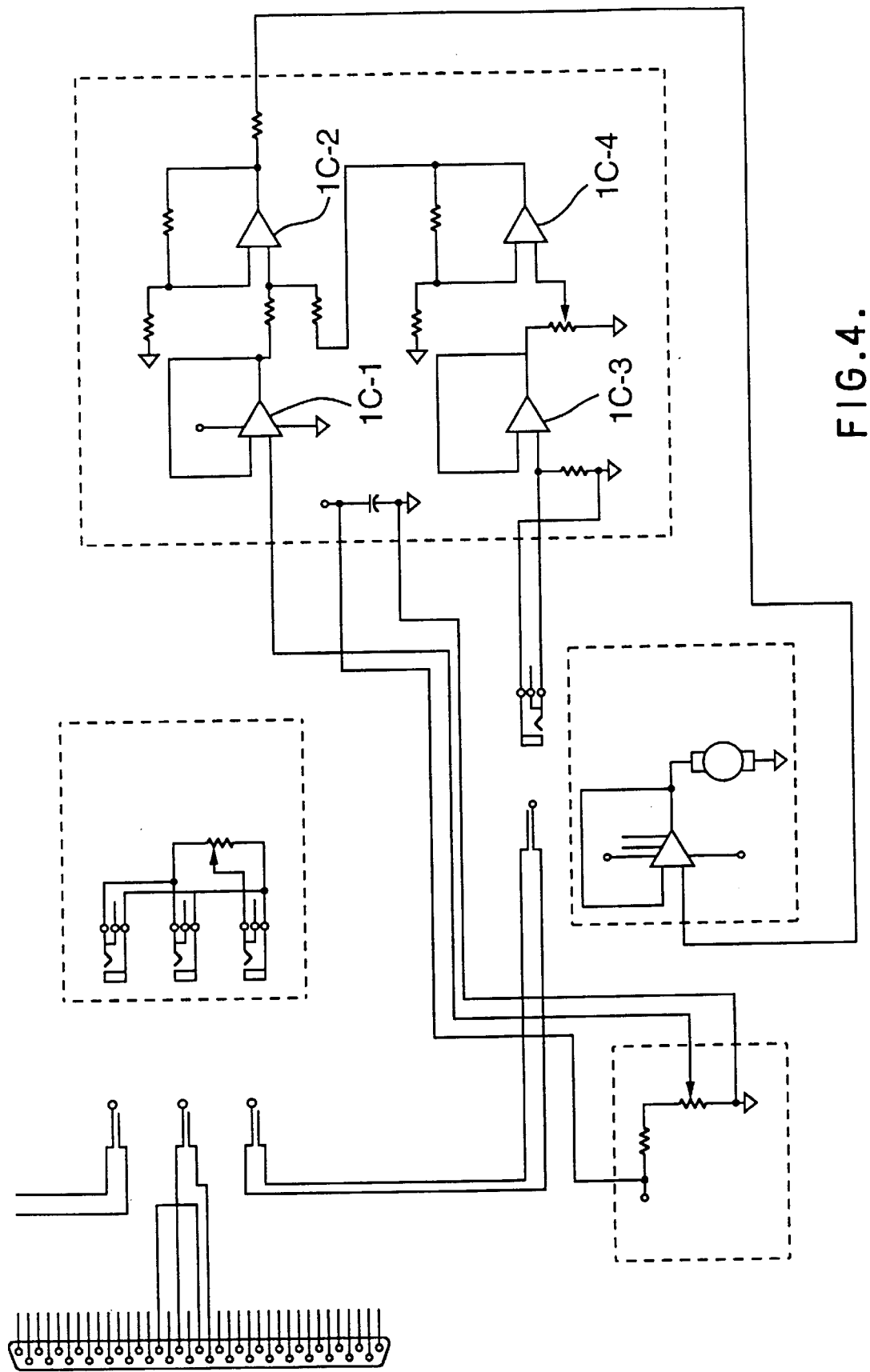
FIG. 4 shows typical circuitry for computer control of a blood pump motor according to the invention.
Figure 5:
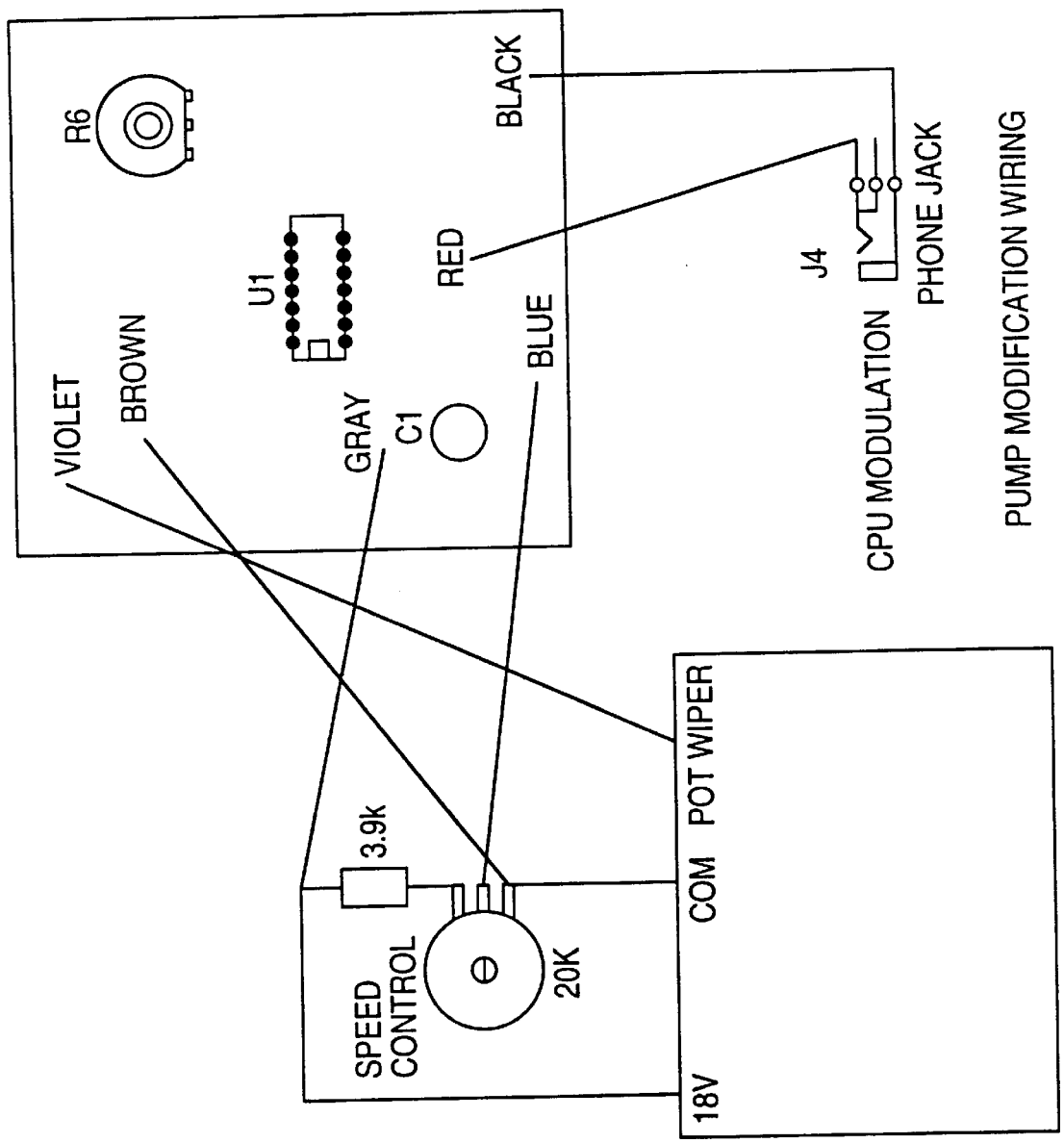
FIG. 5 shows a wiring diagram for a blood pump motor.

Any convenient form of the pump controller may be employed to receive the control signals from the computer and the corresponding voltage signals from the D/A converter. A typical circuitry is shown in FIG. 4 while a wiring diagram appears as FIG. 5. In this circuit, a non-inverting summing amplifier with input buffering is provided, power to operate the amplifier is from the roller pump rate controller. The signal from the original speed control is buffered by a buffer (IC-1), which is applied to one input of a summing amplifier (IC-2). The other input of the summing amplifier is received from the computer modulation signal received from the D/A converter via an external scaling box through buffer IC-3 and amplifier IC-4, which permits an increased voltage range, according to the desired multiple of the amplification, to be applied to the pump servo motor than provided by the D/A converter.

In this way, the roller pump revolutions/min are altered to recreate the pattern of spontaneous biologic variability in the heart function.

The computer operations described above may be effected on any convenient computer hardware programmed in any desired manner to effect the analysis described above to provide the blood pump-control voltage. A program which may be employed, named Purfus, has the listing appearing in Table 1 below.

A configuration file, named Purfus Cfg, is necessary for the operation of Purfus program. This file contains a number corresponding to the base address of the D/A converter card:

| Decimal | Hex |
|---|---|
| 768 | 300 H |
| 784 | 310 H |
| 800 | 320 H |

Figure 6:
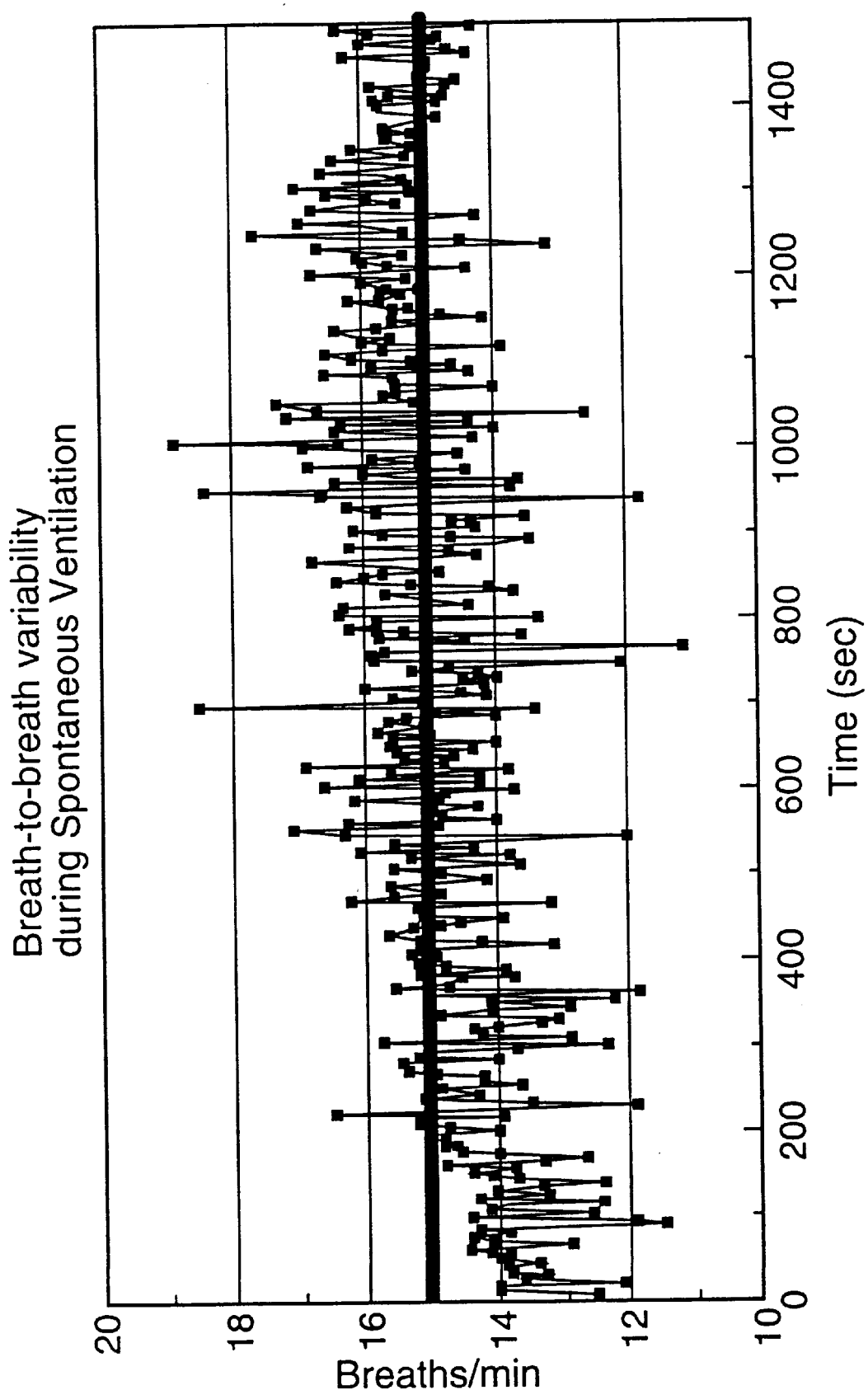
FIG. 6 shows the changes in respiratory rate (breaths/min) over time. Such data is used to create the input file for the ventilator computer controller. These data have a mean rate of 15 breaths/min.

Computer control of a ventilator to apply the principles of the invention thereto may be effected using the computer program shown in Table 2 below. This software allows the 'RATE' and the 'VOLUME' settings of the ventilator controls to be modulated independently via a data file, generated before hand and in a form such as appears in FIG. 6.

In order to implement computer control of the ventilator using the circuitry shown in FIGS. 11 to 17, a means of converting voltage to ventilation 'RATE' and 'VOLUME' is provided. A linear regression analysis of the ventilator's 'RATE' and 'VOLUME' potentiometers output voltage versus dial calibrations is performed ($R^2 = 0.9996$). Functions are converted 'RATE' and 'VOLUME' into voltage, and vice-versa. By control loop scanning the A/D converter channel in the background using the high speed DMA facility, the current setting of the ventilator's 'RATE' control is acquired. If the modulation level for the current time step is greater than the baseline (set by the current setting of the ventilator's 'RATE' control), the D/A converter channel generates a voltage level, which is passed to the summing amplifier in the Ventilator Modulation Unit, necessary to increase the current baseline value of 'RATE' to the modulation level of 'RATE'. The output of the summing amplifier is then sampled by another A/D converter channel, converted into 'RATE', and displayed on the computer screen. The 'VOLUME' are updated in each 'loop' of the control program which executes every 400 milliseconds on a 'control' computer (a 4.77 MHz 8088 processor with a 8087).

EXAMPLES

Example 1

This Example illustrates the methods and materials used in ventilation experiments carried out on pigs.

Pig preparation:

Thirteen (13) pigs weighting 20 to 30 kg were studied. All pigs received atropine 0.6 mg and ketamine 10 mg/kg intramuscularly for induction of anesthesia. Once sedated, isoflurane in oxygen was administered by face mask. When airway reflexes had been obtunded, the pig was intubated with a 6.0 mm endotracheal tube. Mechanical ventilation was instituted with an Ohio 7000 anesthesia ventilator at 15 breaths/min with the minute ventilation adjusted to maintain the end-tidal $CO_2$ at 35 to 40 mm Hg. Isoflurane was administered at 2.0 percent end-tidal in oxygen during surgical preparation. Lactated Ringer's was infused IV at 10 ml/kg/hr during the experiment. Pancuronium bromide was administered IV intermittently for muscle relaxation.

The animal was turned supine and a cutdown performed in the groin. A double-lumen catheter was placed in the femoral artery for intermittent sampling of blood for arterial blood gases (ABG) and continuous recording of arterial pressure. A 7.5 Fr pulmonary artery catheter was inserted via the femoral vein and advanced with the balloon inflated until a pulmonary capillary wedge pressure (PCWP) was obtained. Pulmonary artery pressure was continuously recorded. Mixed venous blood was sampled from the distal end of the pulmonary artery catheter. Cardiac output (CO) was measured intermittently, by thermodilution, following 5 ml injection of room temperature saline (performed in triplicate). Following surgery, the animal was allowed to stabilize for 30 minutes and the isoflurane concentration was reduced to 1.5 percent end-tidal.

Baseline hemodynamic and respiratory measurements were then obtained. These included measurements of mean arterial pressure (MAP), mean pulmonary artery pressure (MPAP), PCWP, airway pressures at the proximal end of the endotracheal tube (all recorded to a Gould 2600 oscillograph and to an advanced CODAS data acquisition system), and CO. Gas measurements included arterial and mixed venous blood gases and end-expired gas sampled from the expiratory limb of the anesthesia circuit. These were measured using a Radiometer ABL3. Arterial and mixed venous oxygen content, oxygen saturation and hemoglobin concentration were measured with a Radiometer OSM3 set for porcine blood. All measurements were obtained in duplicate. Calculated indices included pulmonary vascular resistance (PVR), dead space ventilation (VD/VT) and shunt fraction (QS/QT).

Oleic Acid Lung Injury: After the above measurements were obtained a Valsalva maneuver was done (mean airway pressure 30 cm $H_2O$ for 5 seconds). An infusion of oleic acid was started at 0.2 ml/kg/hr through the infusion port of the pulmonary artery catheter. At 5 min intervals the Valsalva maneuver was repeated and 1 min later an arterial blood gas obtained. The oleic acid infusion was continued until the $PaO_2$ decreased to $\leq 200$ mm Hg for 2 consecutive measurements. At this point the infusion was stopped and the volume infused noted. Following repeat hemodynamic and respiratory measurements as above, the animals were randomly allocated to one of two ventilatory modes; conventional IPPV with the respiratory rate (RR) fixed at 15 breaths/min with the minute ventilation (MV) changed to maintain $PaCO_2$ at $\leq 45$ mm Hg (control), or IPPV with a computer-controller with variable RR but with a mean of 15 breaths/min (computer). Again, MV was adjusted to maintain $PaCO_2$ at $\leq 45$ mm Hg. Ventilation continued with either the control or computer mode for the duration of the experiment. Every 30 minutes for 180 min, hemodynamic and respiratory data was obtained as above in duplicate. At 180 min, airway pressure data was acquired to the data acquisition system over a 2 min time period to sample approximately 30 consecutive breaths.

Figure 9:
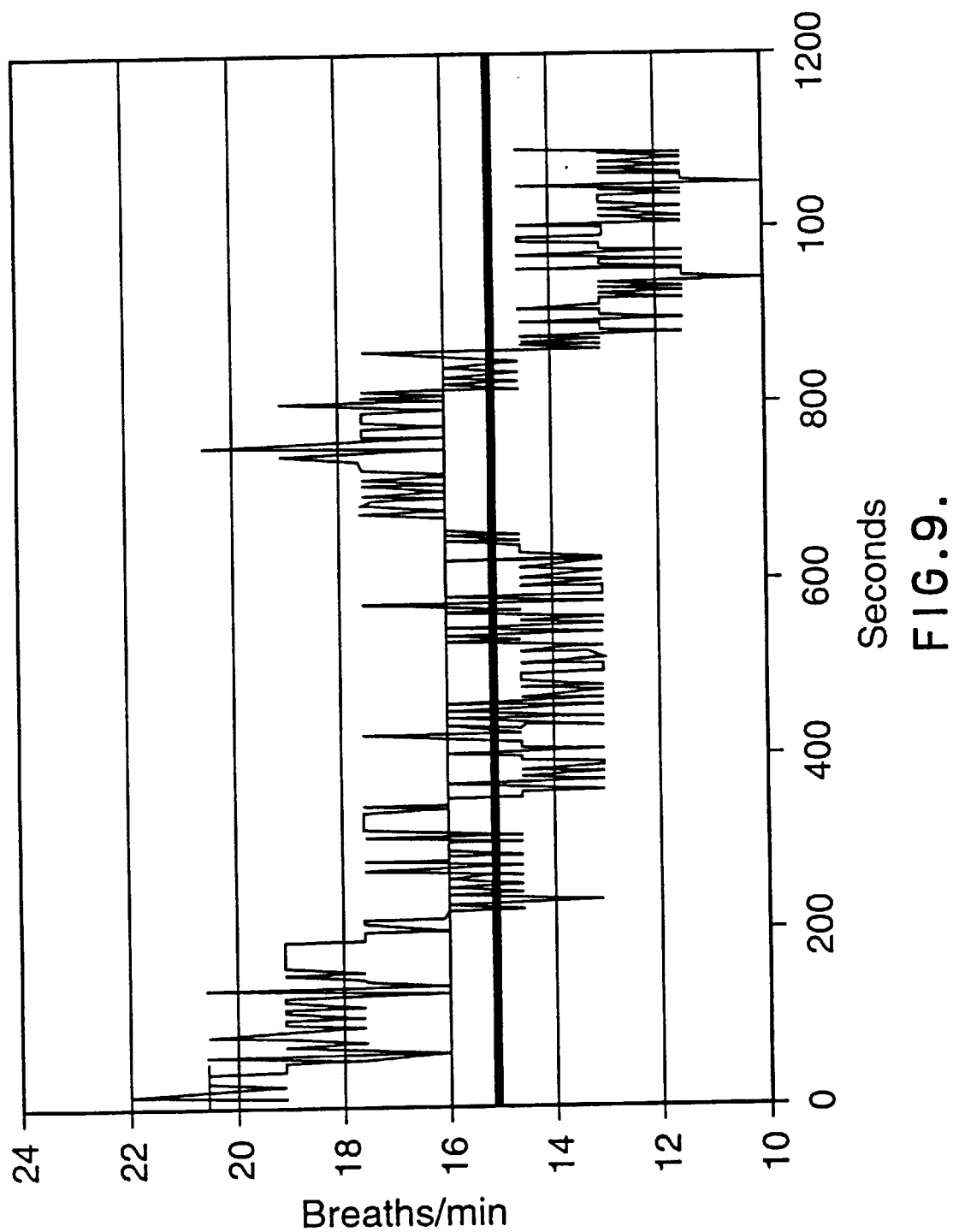
FIG. 9 is similar to FIG. 6 and shows the changes in respiratory rate (breathes/min) over time as well as the mean value.
Figure 10:
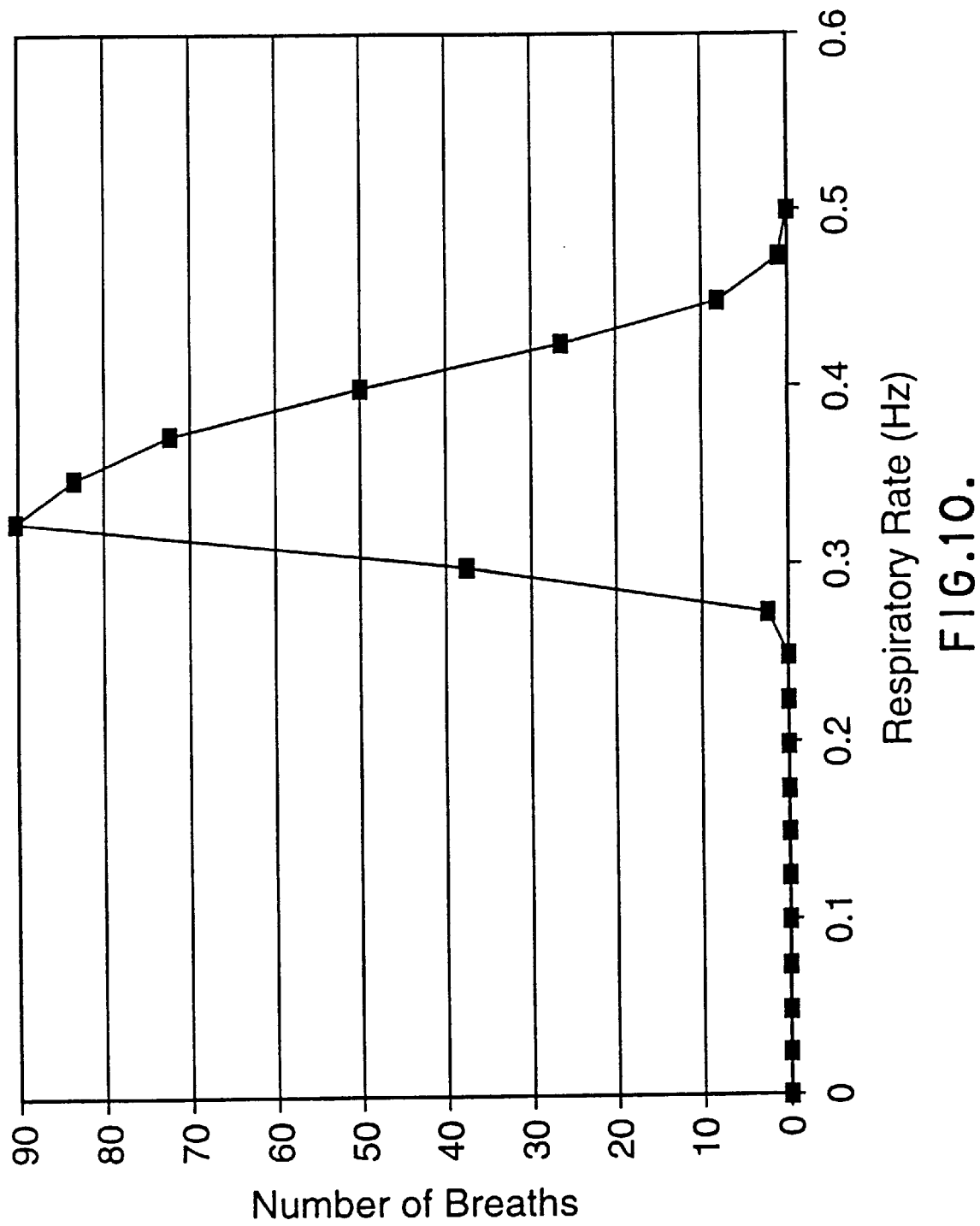
FIG. 10 shows a frequency vs respiratory rate plot devised from the graph of FIG. 9.
Figure 11:
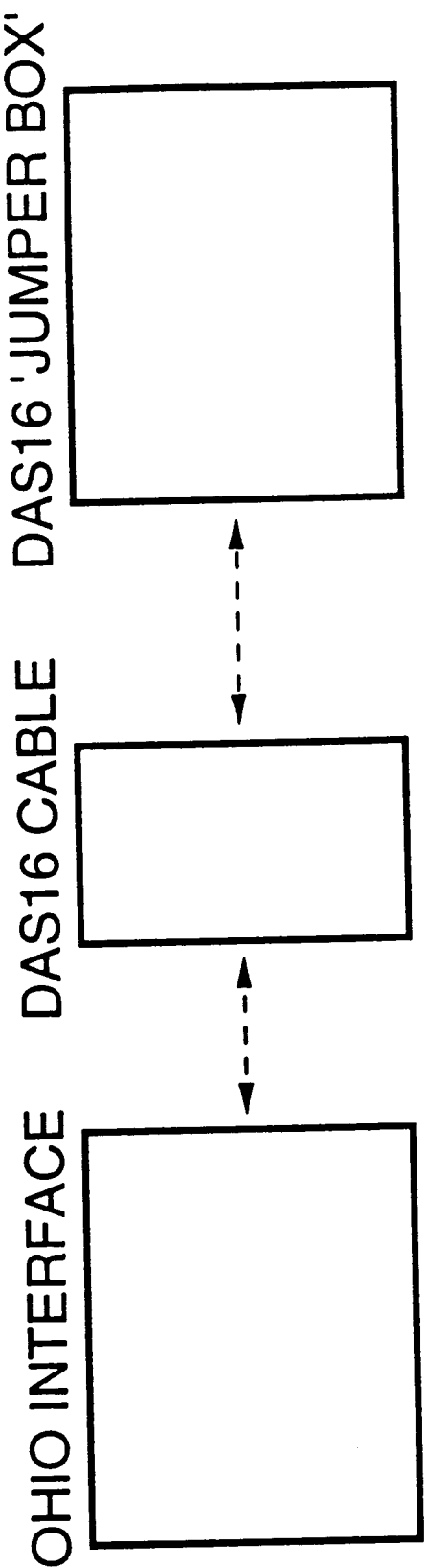
FIG. 11 is a block diagram showing the overall signal flow to the ventilator (Ohio 7000) used in the Examples described below. The 'Ohio Interface' module is connected to the Metrabyte DASH16 analog to digital (A/D) converter via bi-directional control lines via the 'DAS16 Cable' and 'DAS16 Jumper Box'.
Figure 12A:
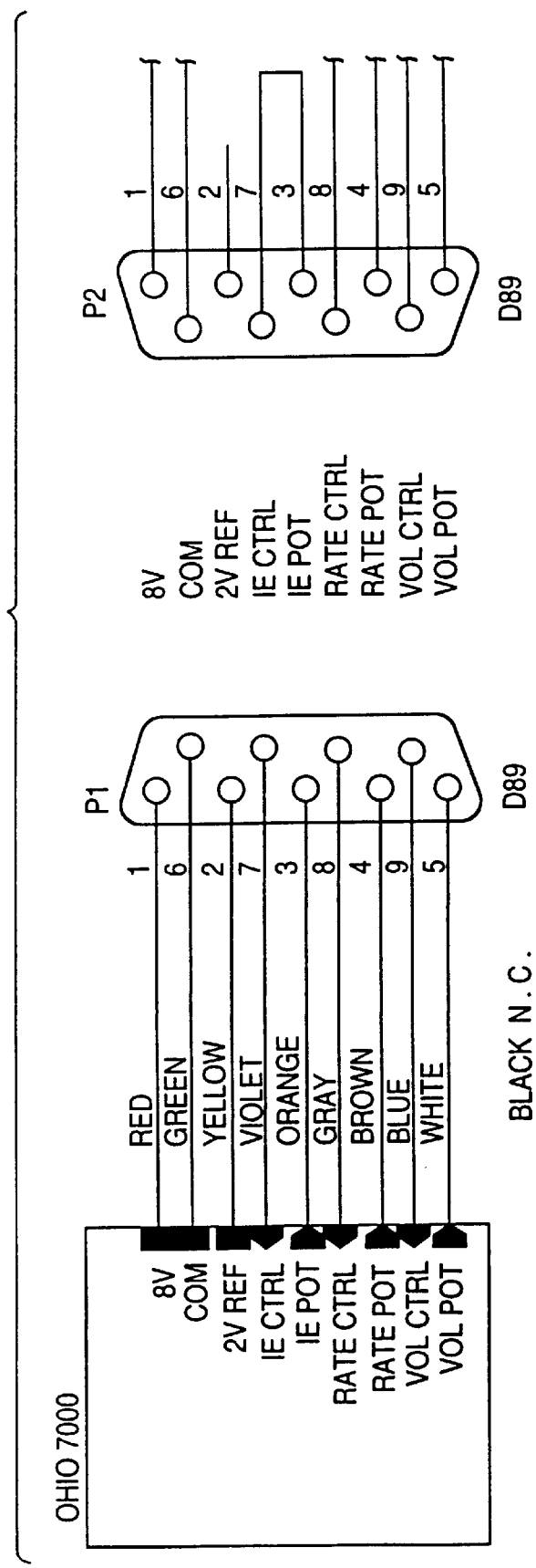
FIG. 12 is the internal wiring harness of the Ohio Interface Unit. Connector 'P1' and module 'Ohio 7000' refer to the cable and modifications added to the Ohio 7000 Ventilator. This Figure shows all physical wiring connections of the electronic modules ('Volume Modulator' and 'Rate Modulator') to the switches and connectors. The Ohio 7000 supplies the power (8V & COM). Connectors 'P2' and 'P3' are opposite gender. Experimental monitoring jacks ('J1' through 'J4') are for an external data acquisition system. Connector 'P3' interfaces to the Metrabyte model DASH16 A/D and digital to analog (D/A) converter. Switch S1 and S2 provide the ability to cancel 'RATE' or 'VOLUME' modulation individually ('manual' position) at any time.
Figure 12B:
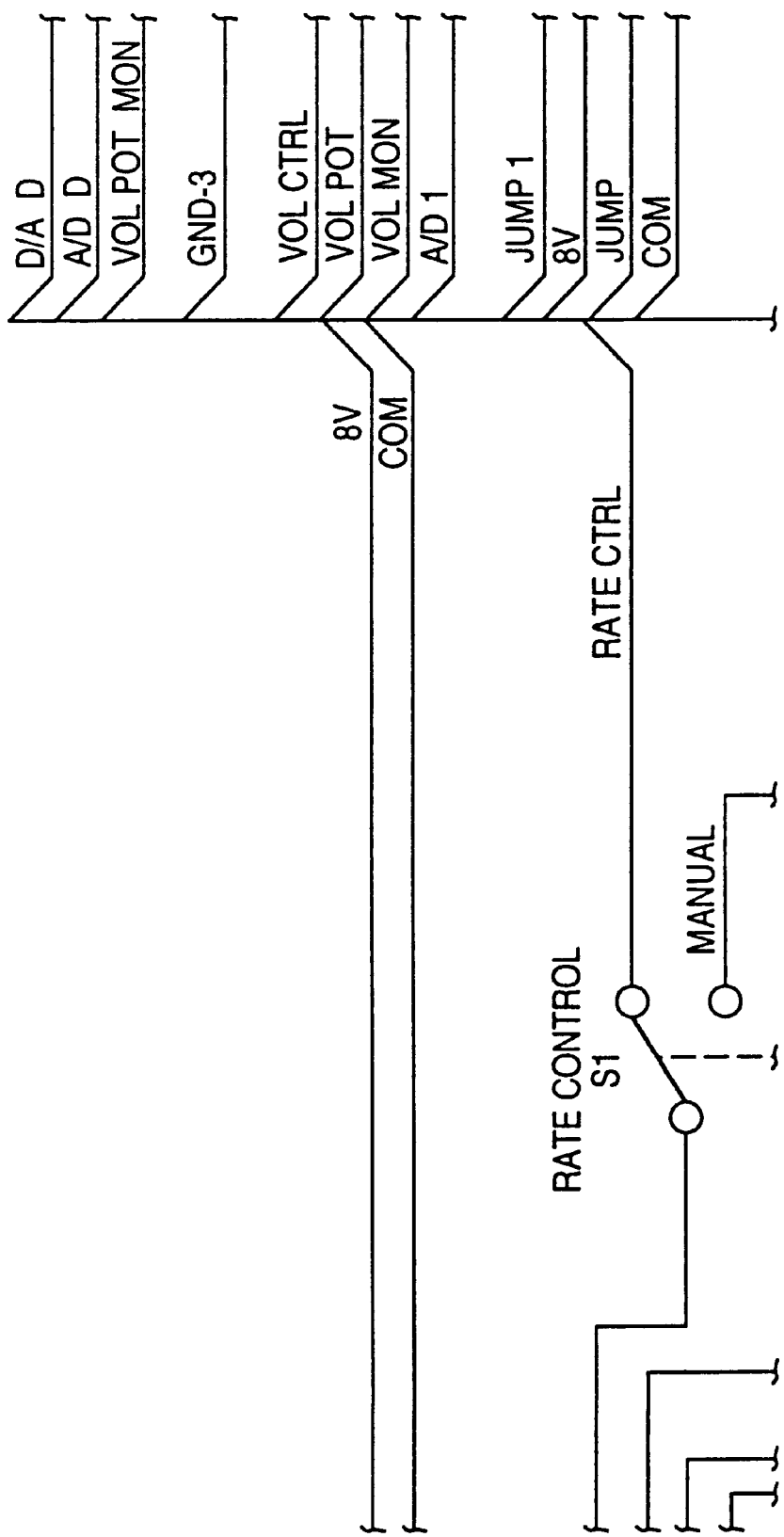
Figure 12C:
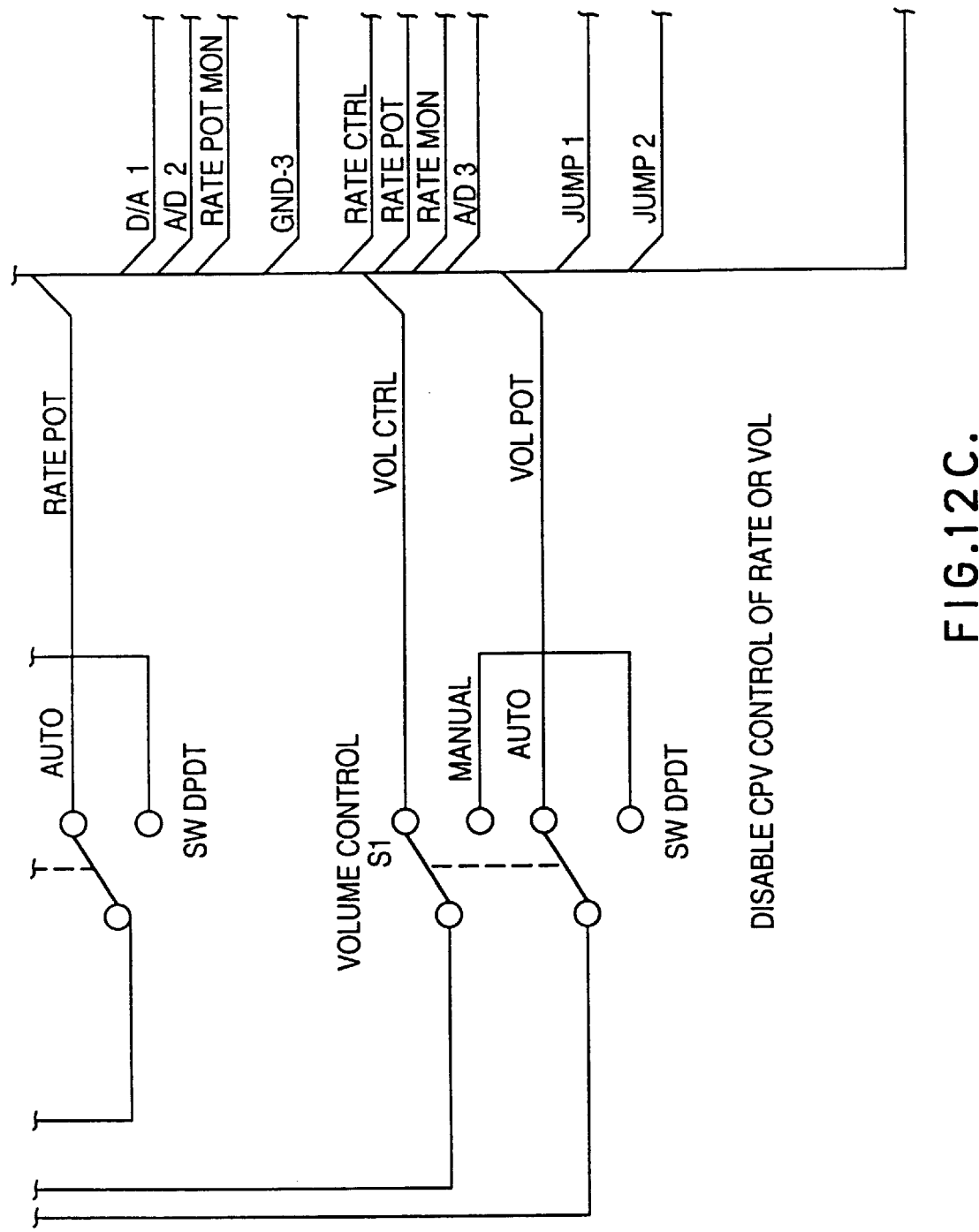
Figure 12D:
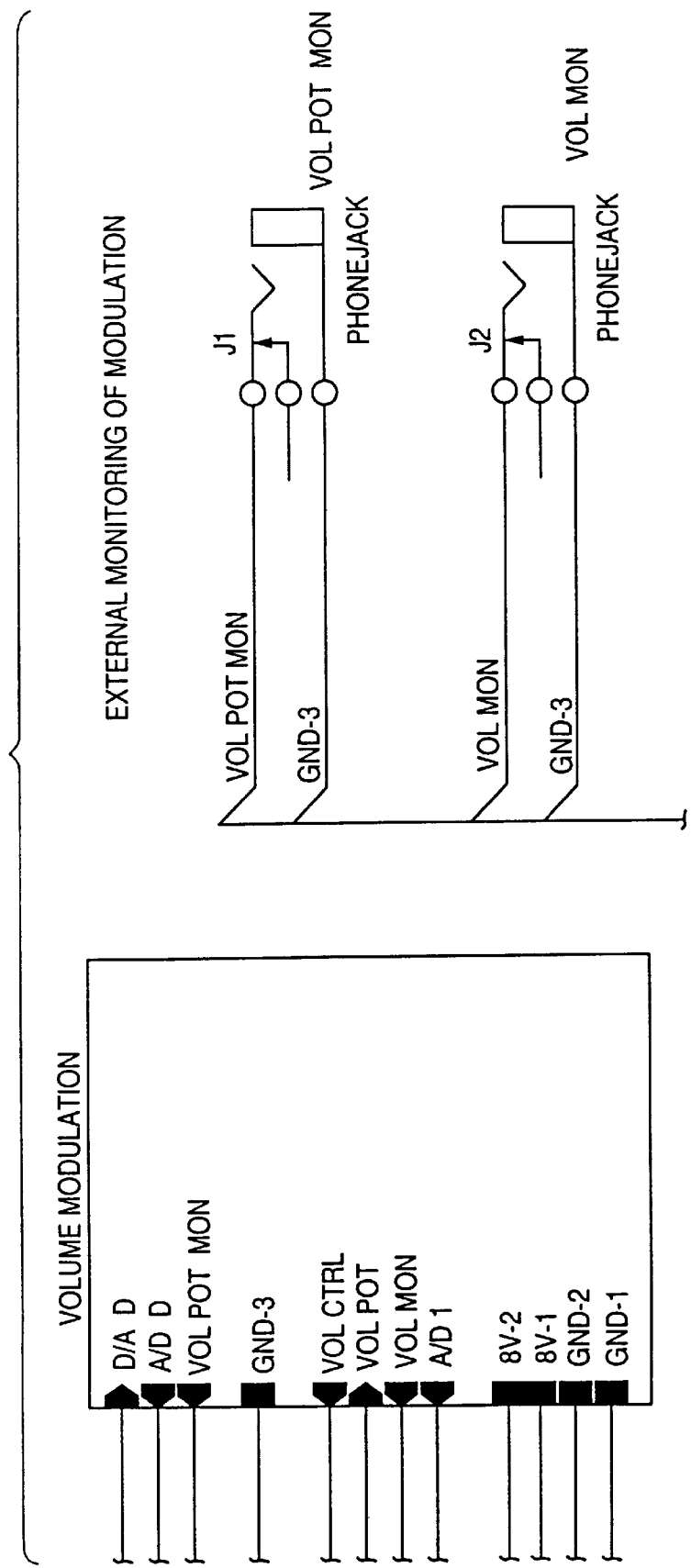
Figure 12E:
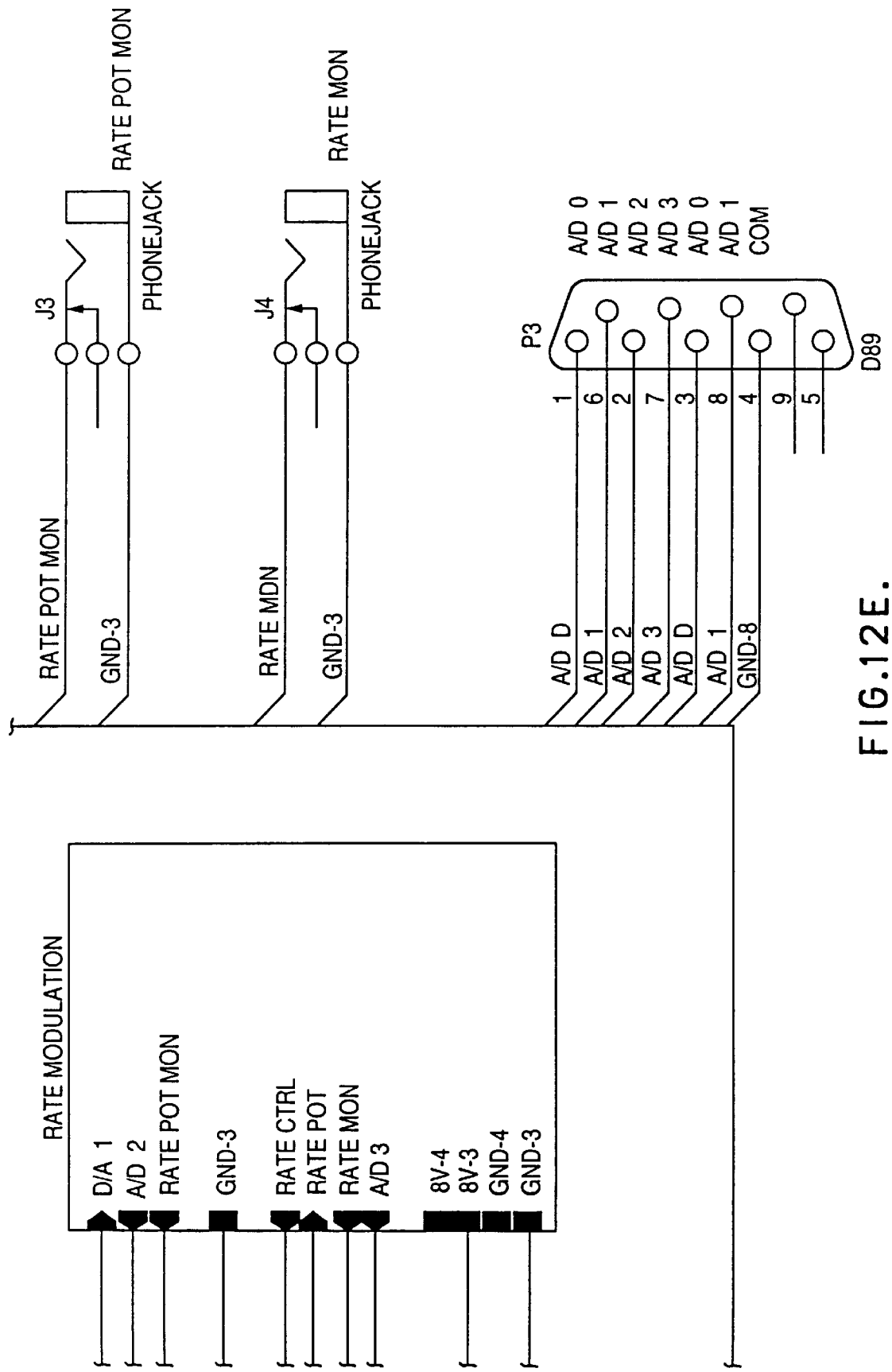
Figure 13A:
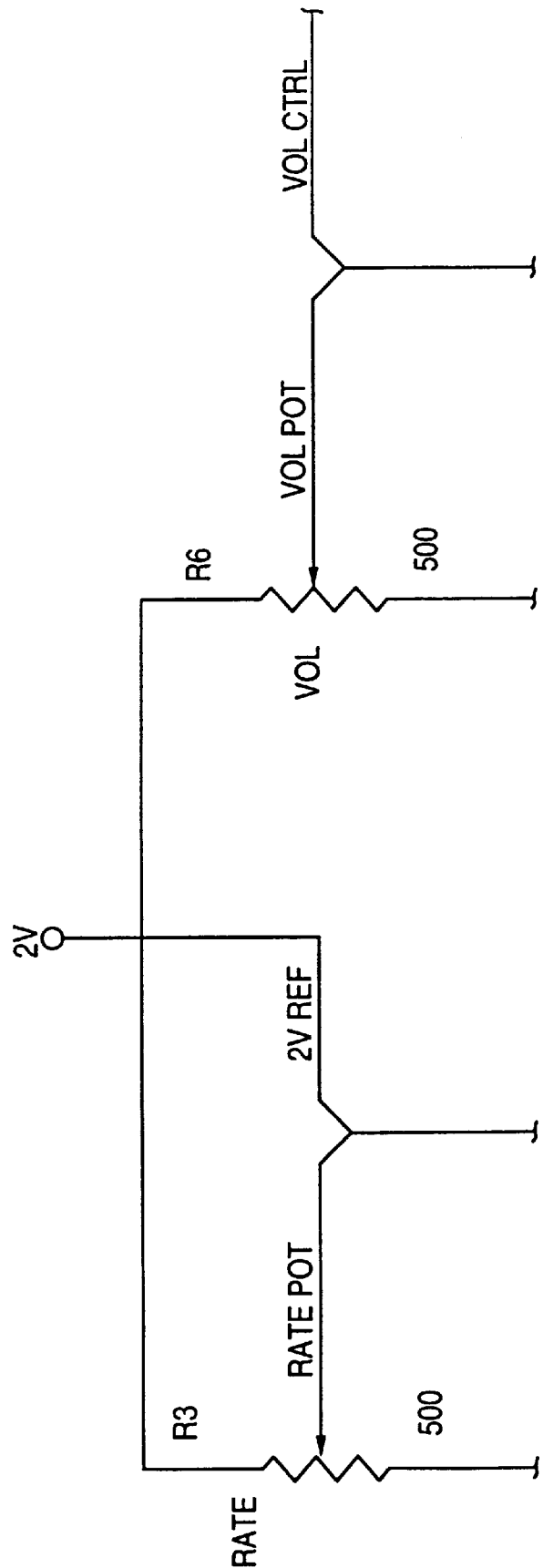
FIG. 13 displays an excerpt of the Ohio 7000 Ventilator control circuitry generated with an ohm meter and a photocopy of the service manual. Refer to the 'IE' ratio control R14. The control's wiper was originally connected to amplifier U22B. Modulation of the 'IE' control is introduced by inserting an external summing amplifier between the control and amplifier U22B (pins 3 and 7 of connector P4). Similarly, the 'RATE' and 'VOLUME' controls and their associated amplifiers (U22A and U5D) are routed to P4 pins 4 and 8, and 5 and 9 respectively. The 2 volt reference voltage for the 'RATE' and 'VOLUME' controls, as well as 8 volt supply and common are also routed to connector P4. Referring back to connector P2 in FIG. 12: external modulation of 'IE' was disabled (pins 3 and 7 jumpered), and the 2 volt reference (pin 2) was not required.
Figure 13B:
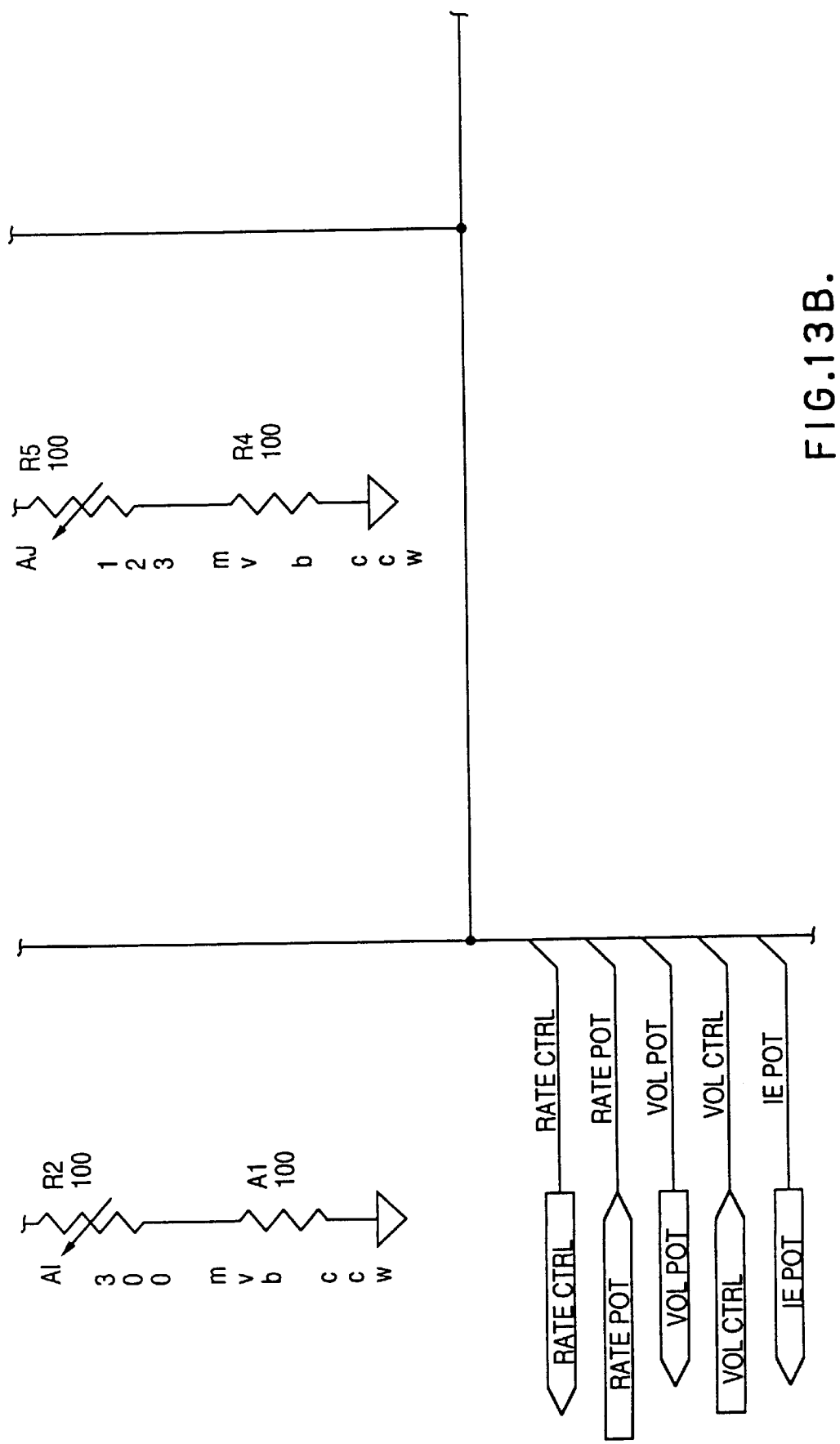
Figure 13C:
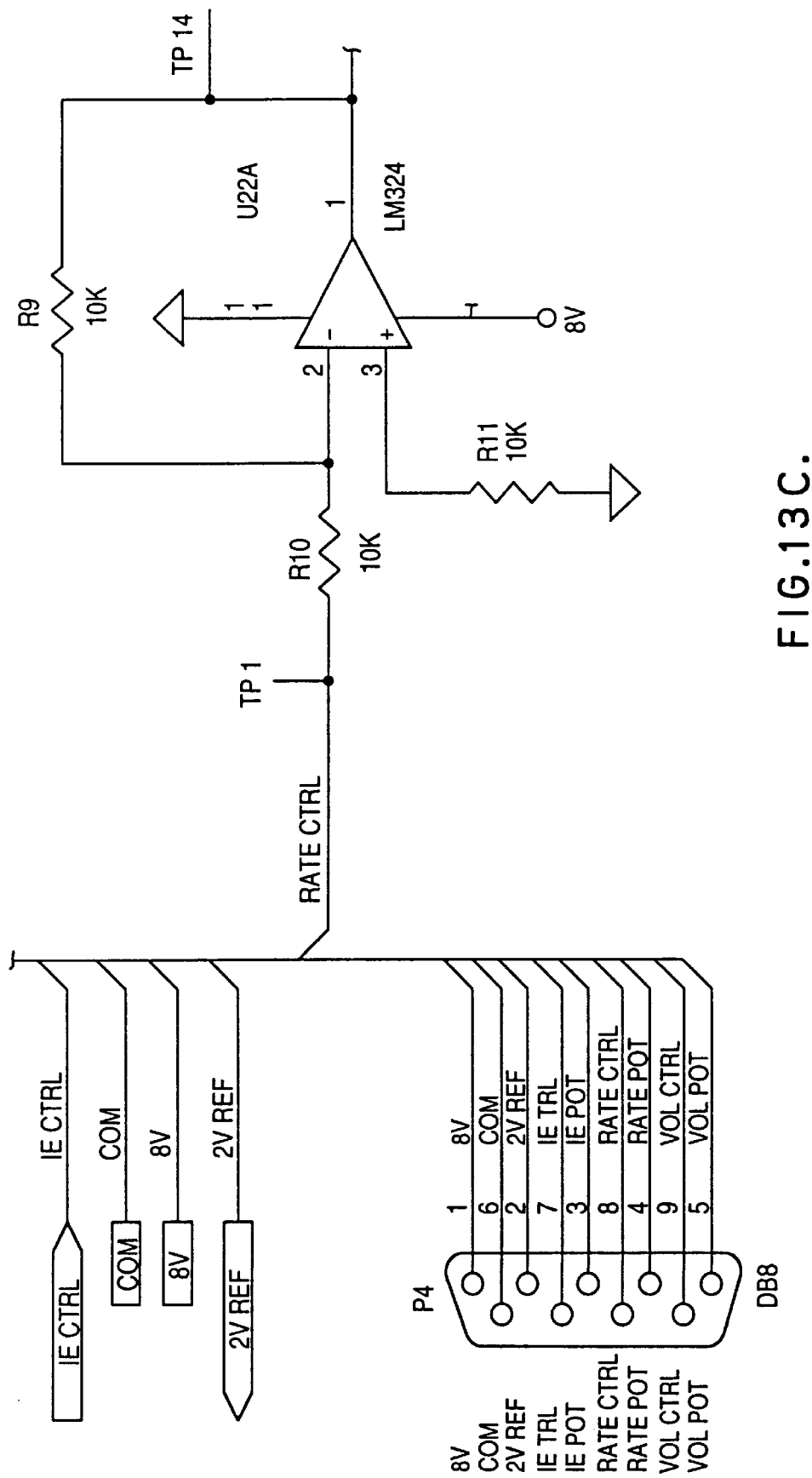
Figure 13D:
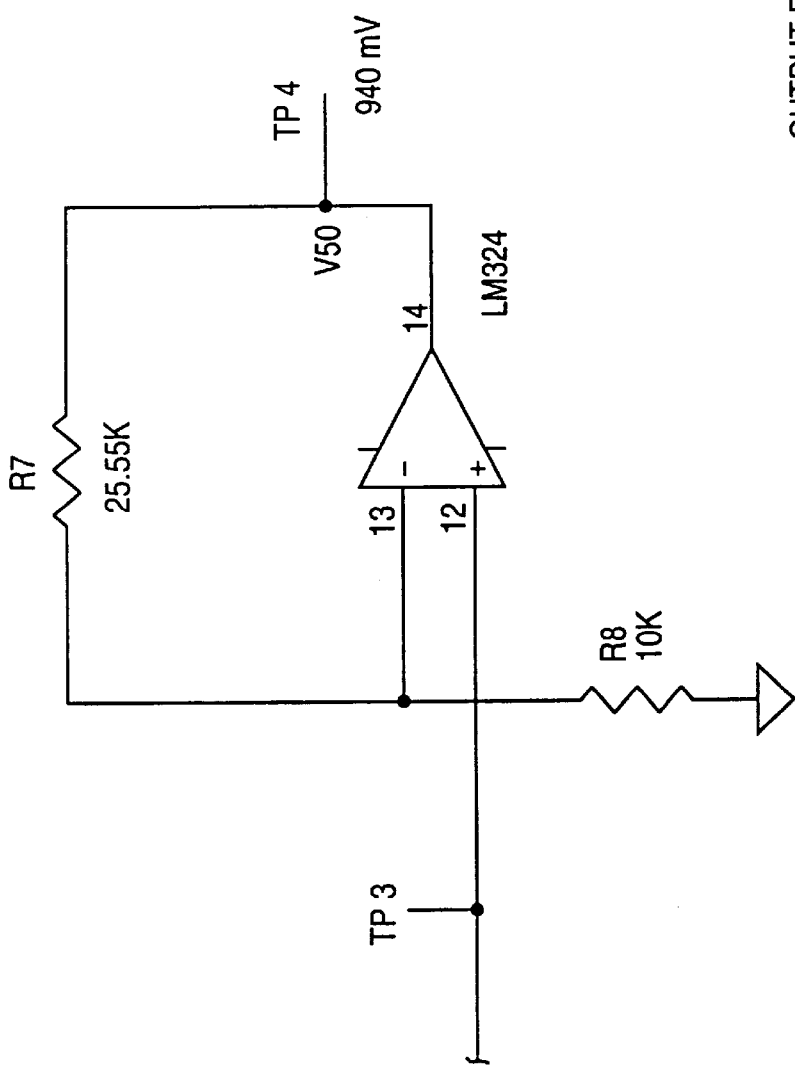
Figure 13E:
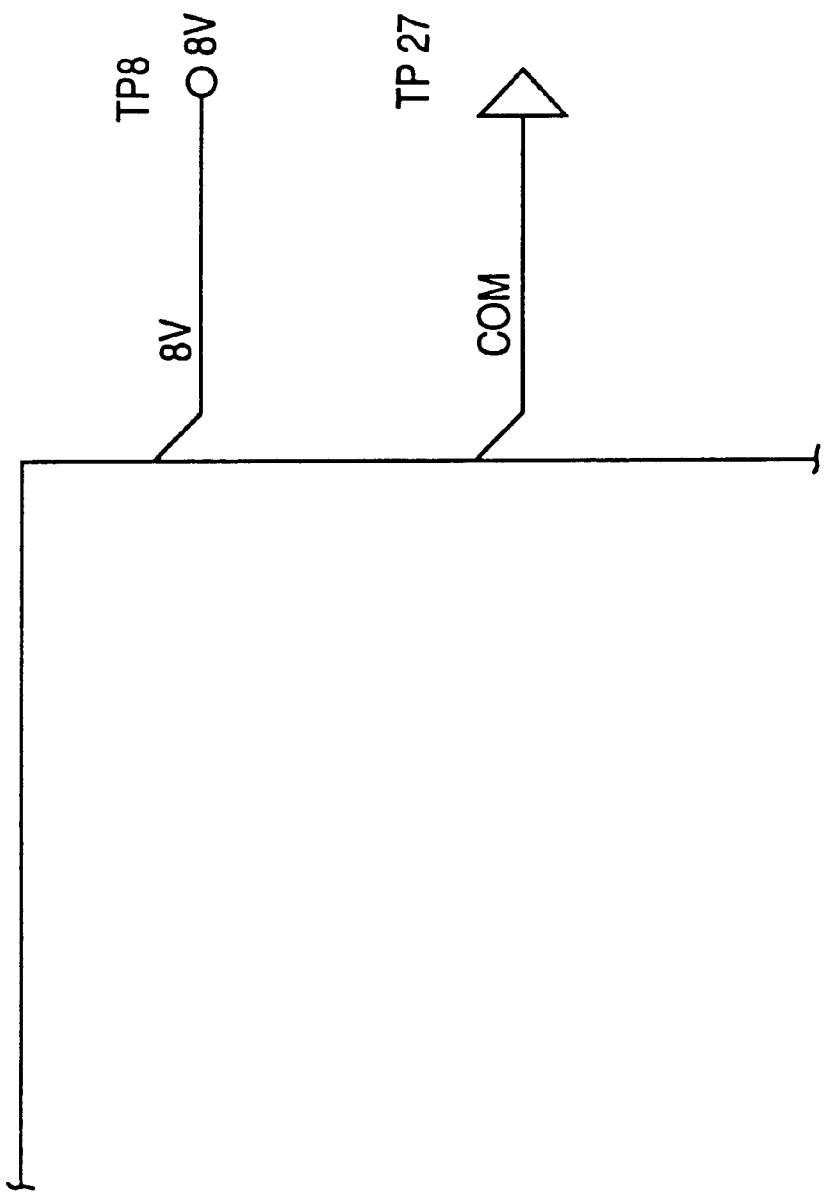
Figure 13F:
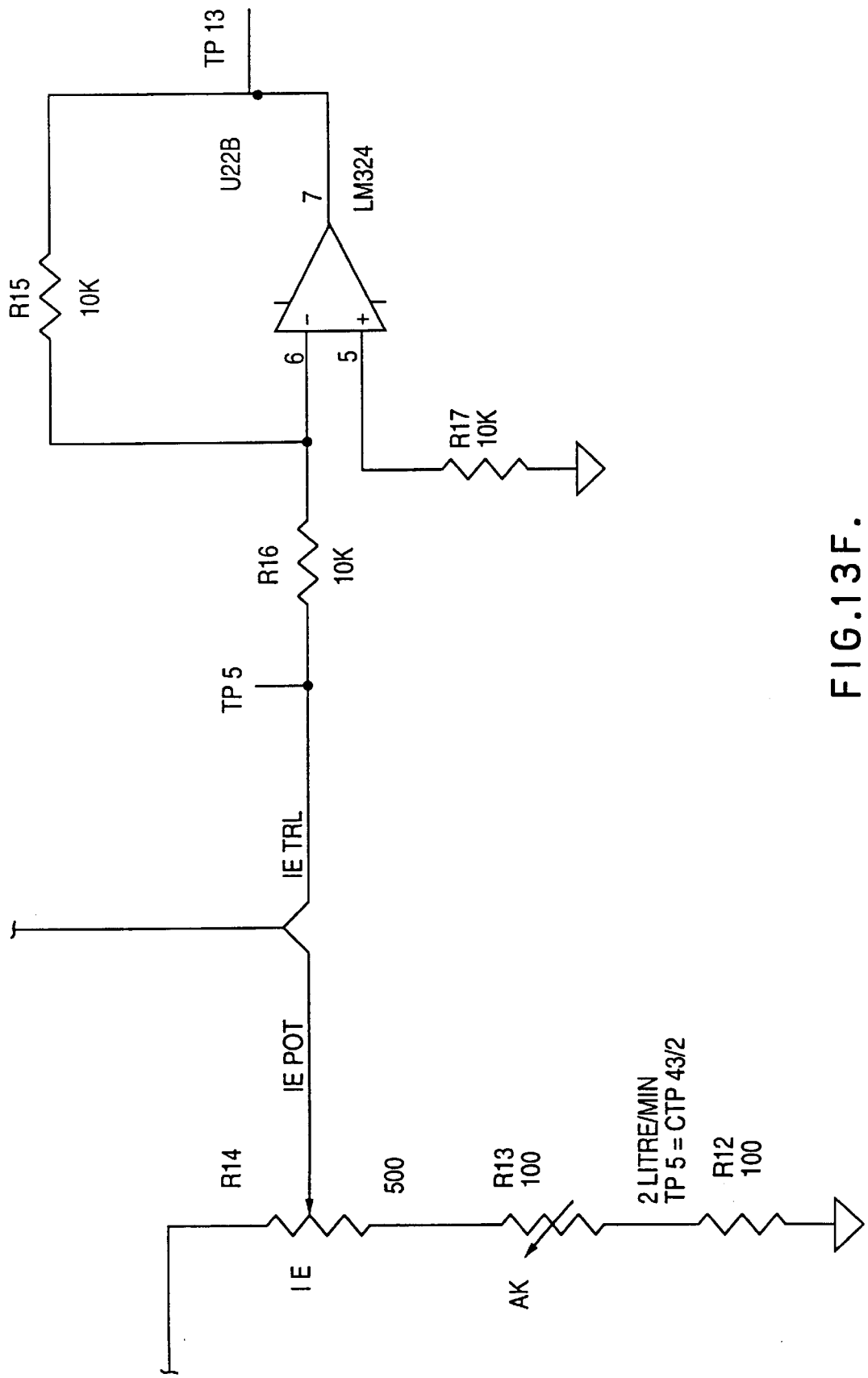
Figure 14A:
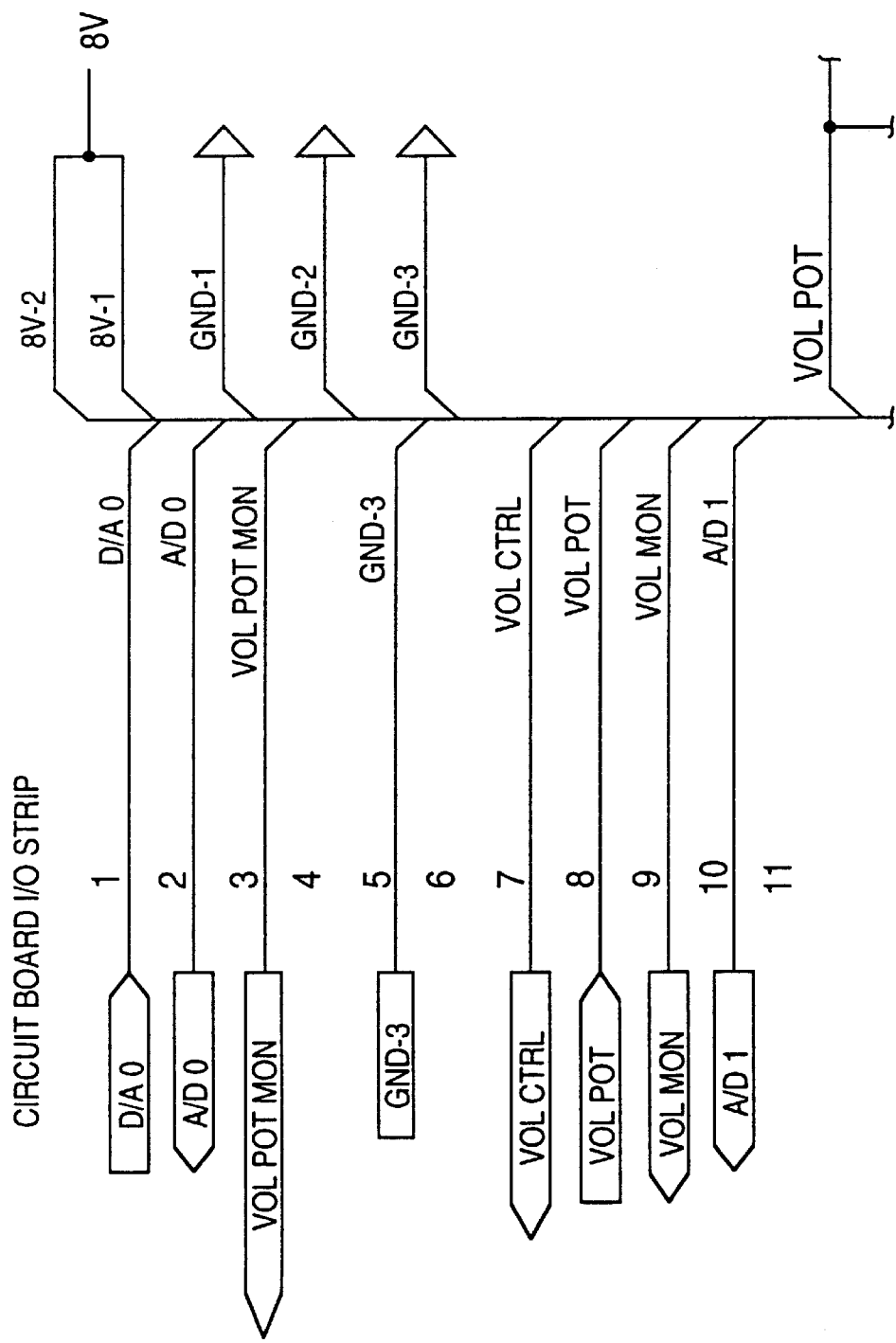
FIGS. 14 and 15 display the modulation control electronics for 'VOLUME' and 'RATE' respectively. The circuit boards are interchangeable.
Figure 14B:
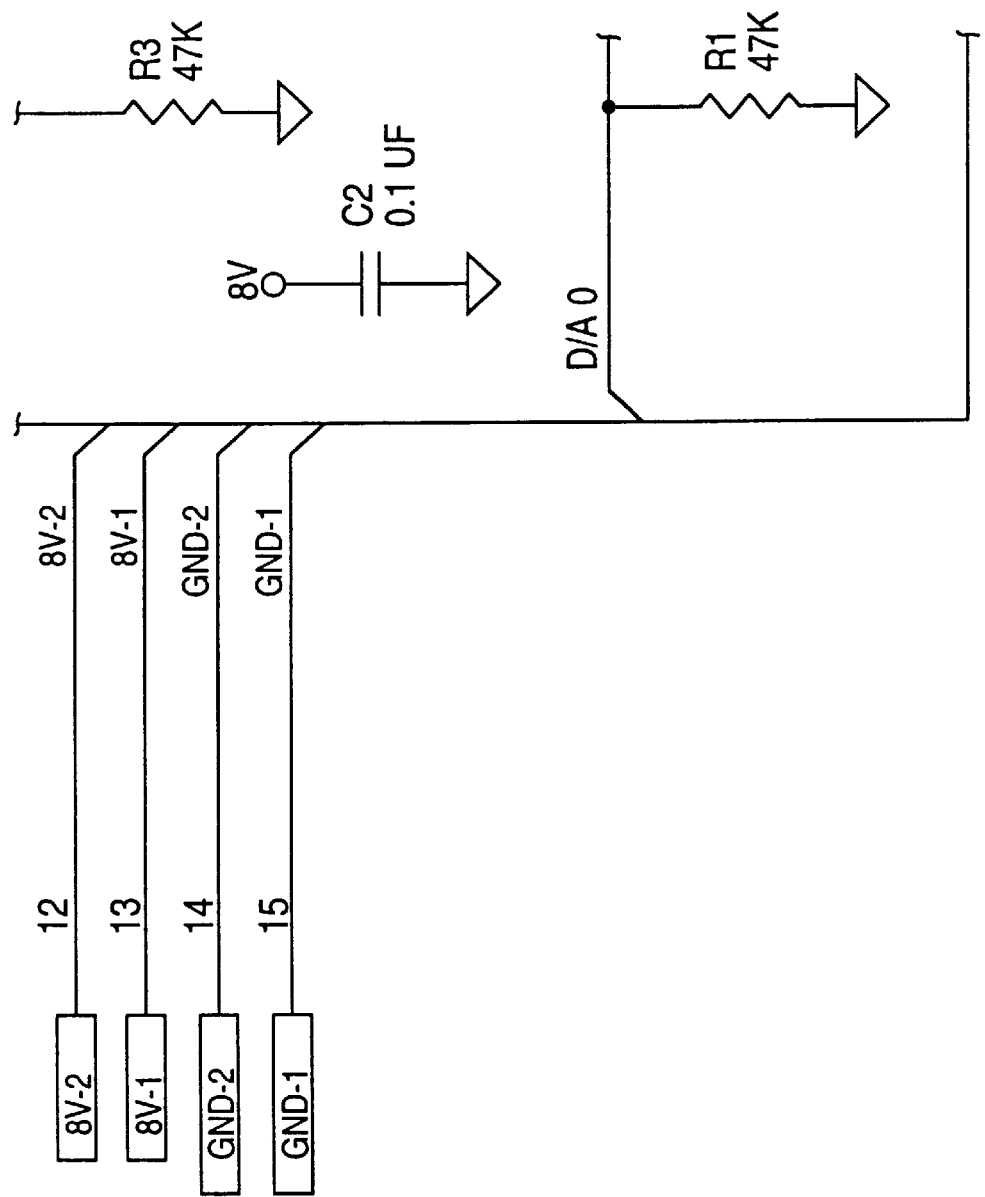
Figure 14C:
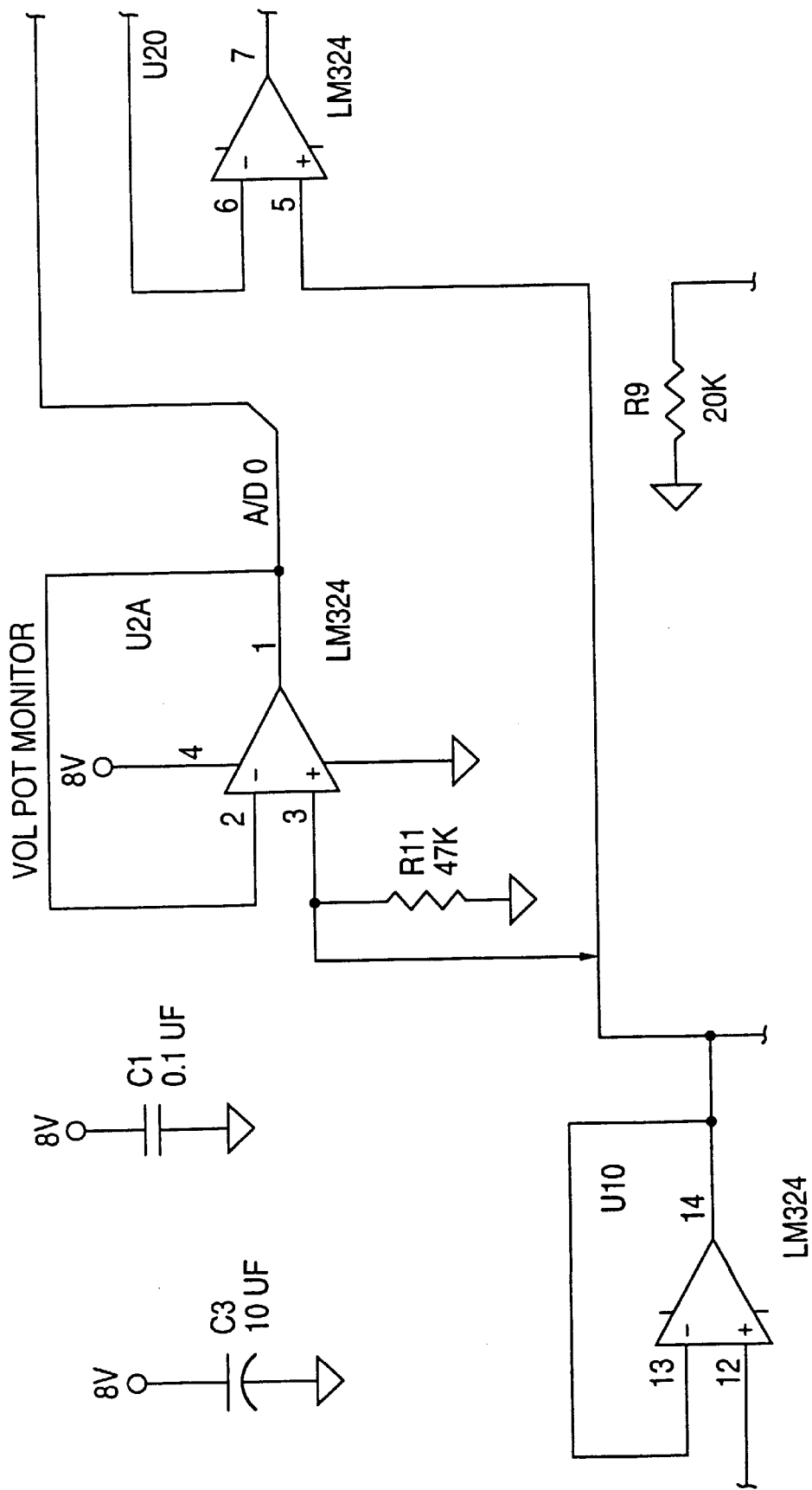
Figure 14D:
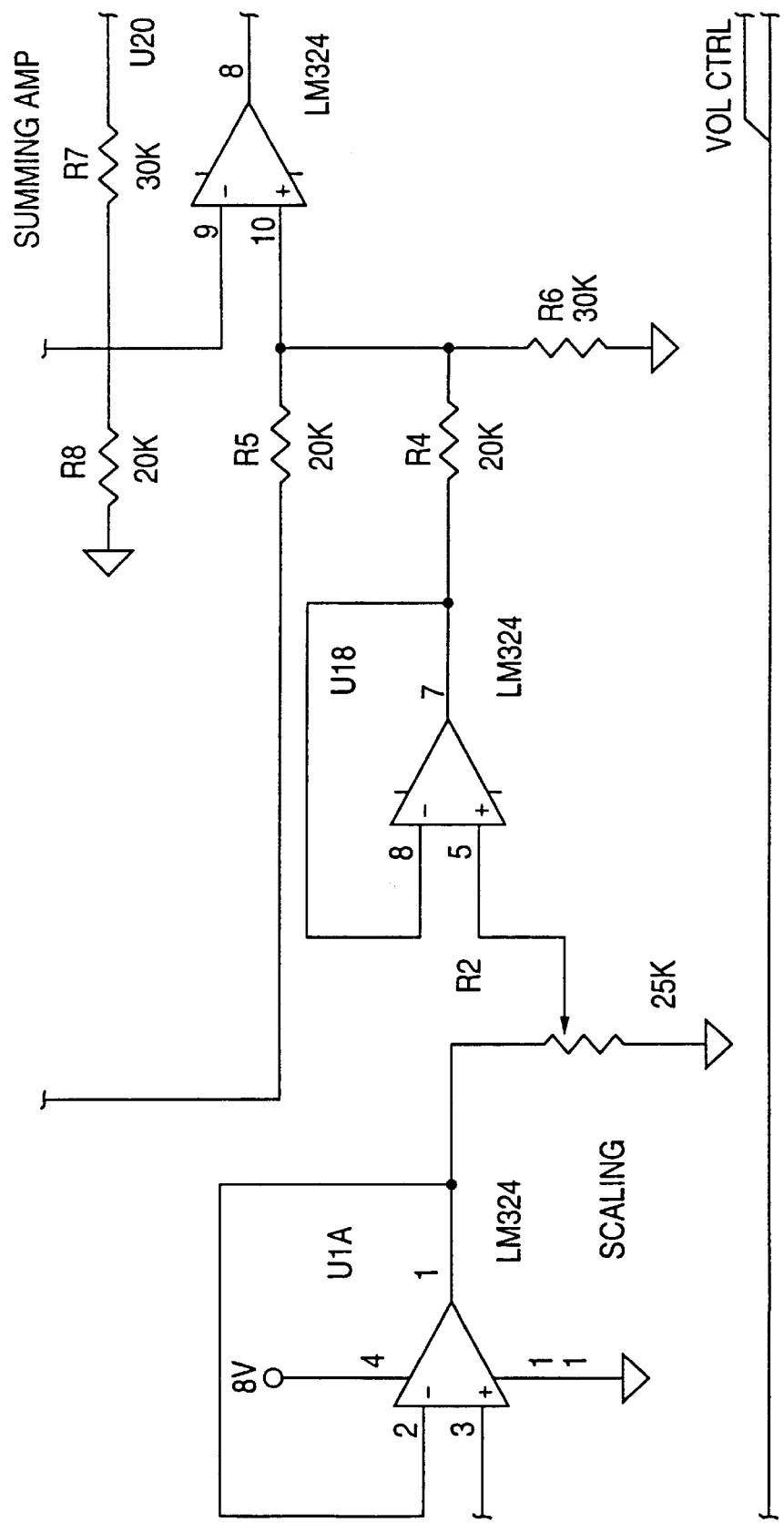
Figure 14E:
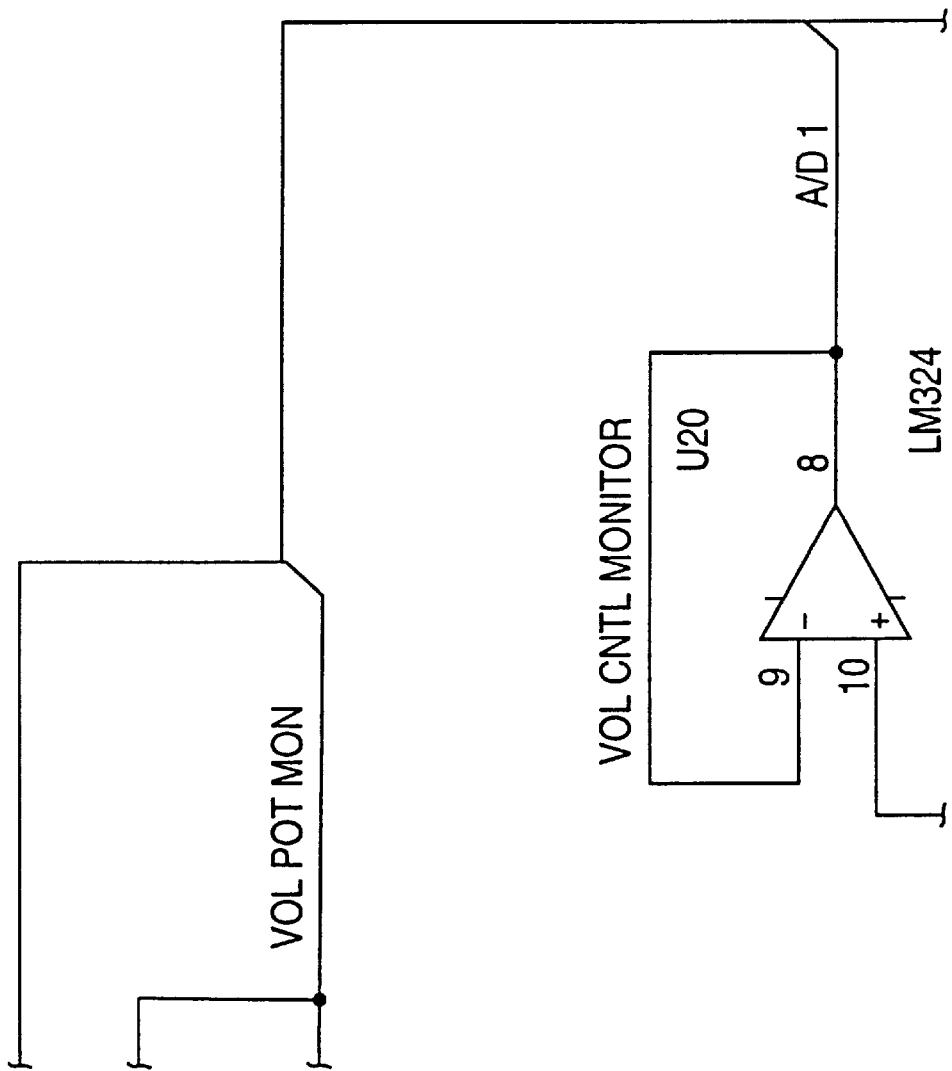
Figure 14F:
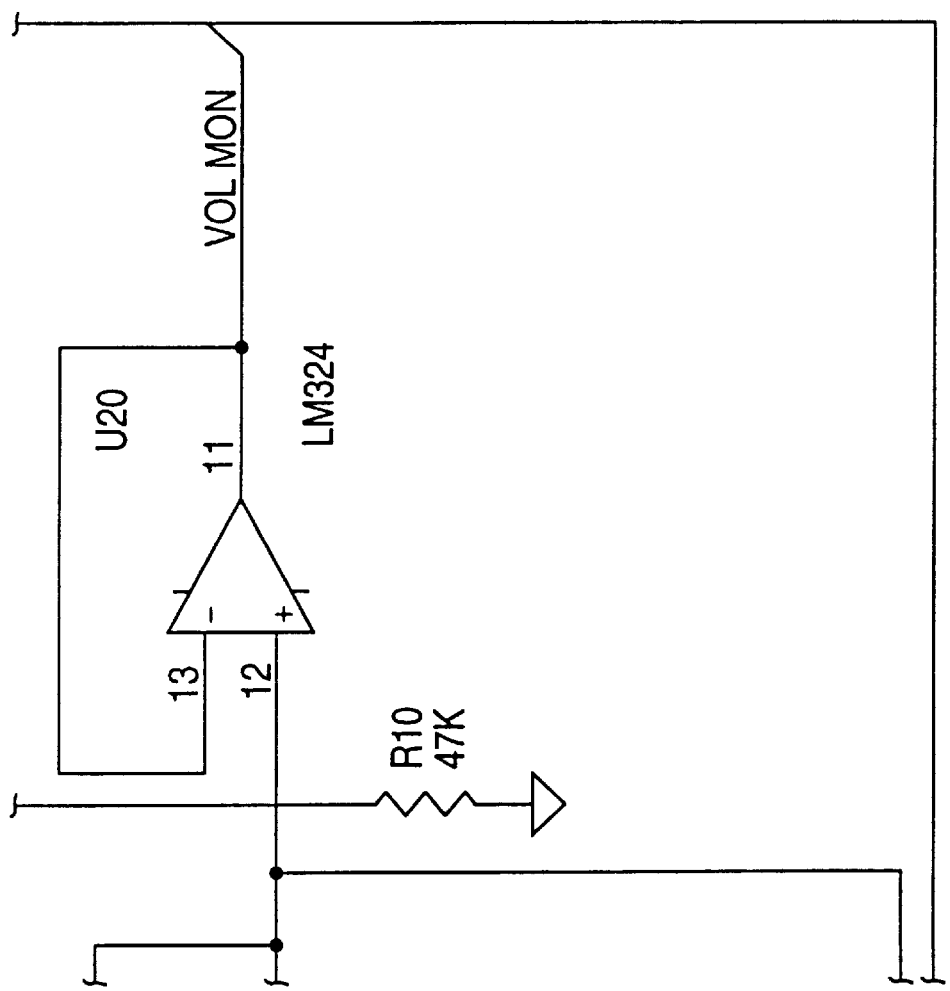
Figure 15A:
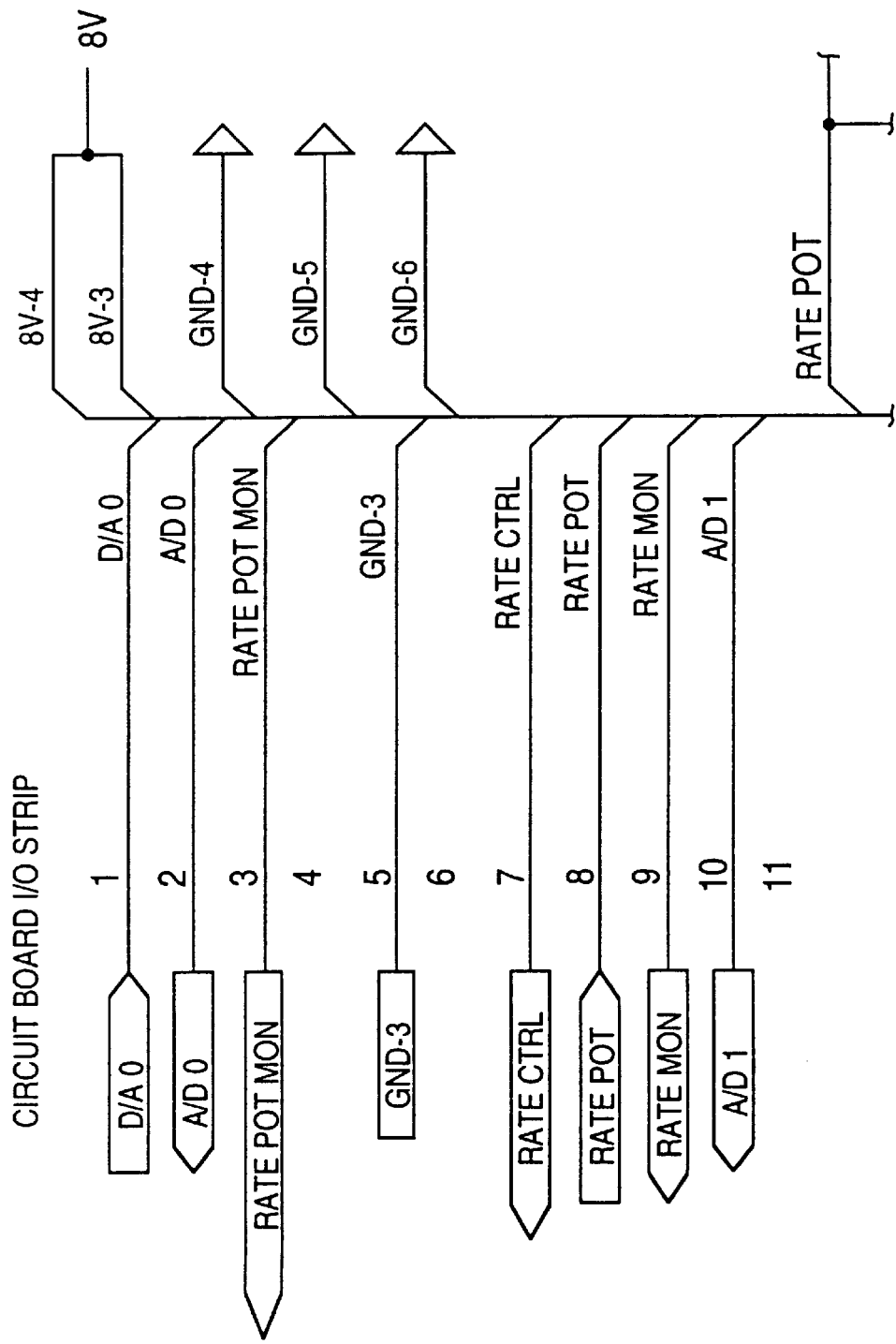
Figure 15B:
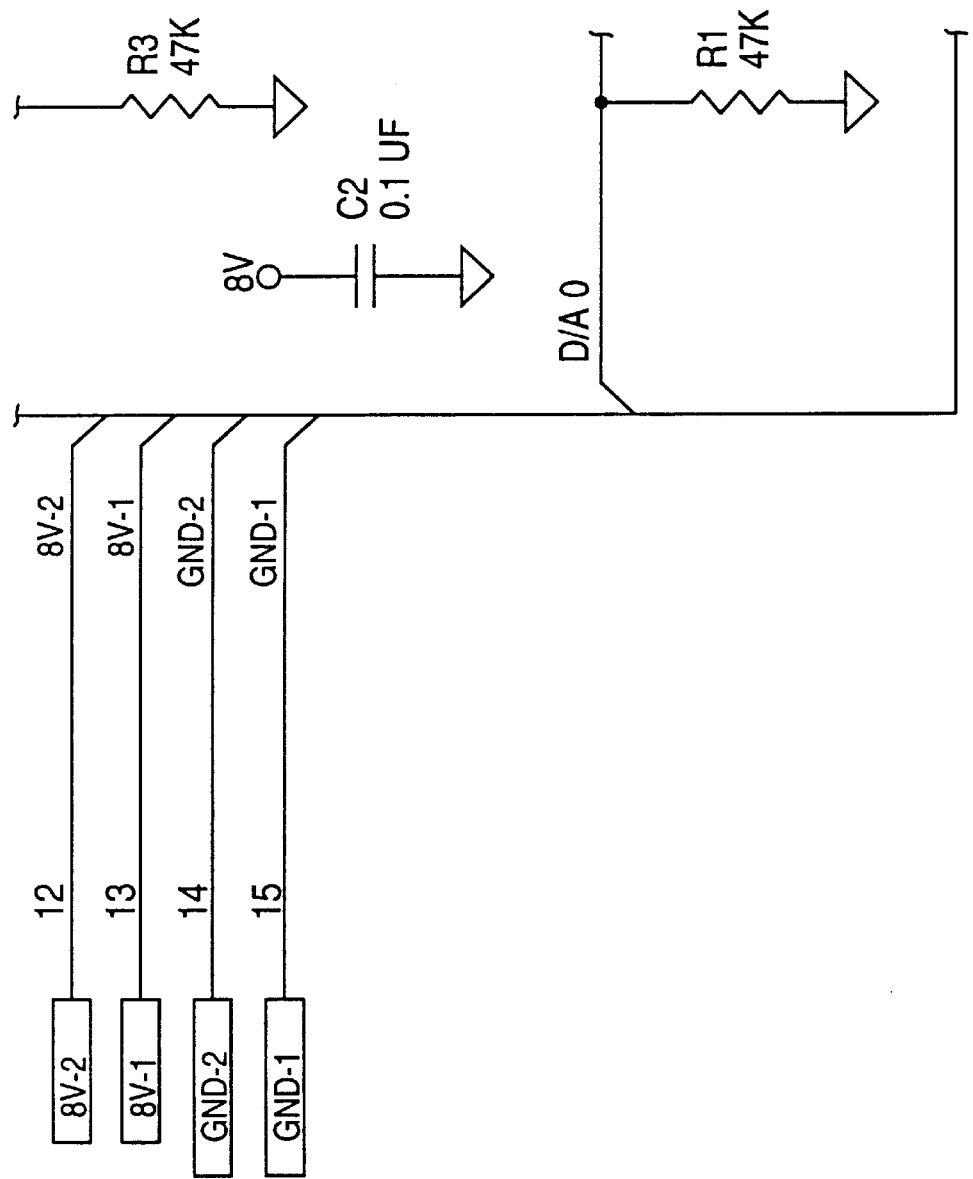
Figure 15C:
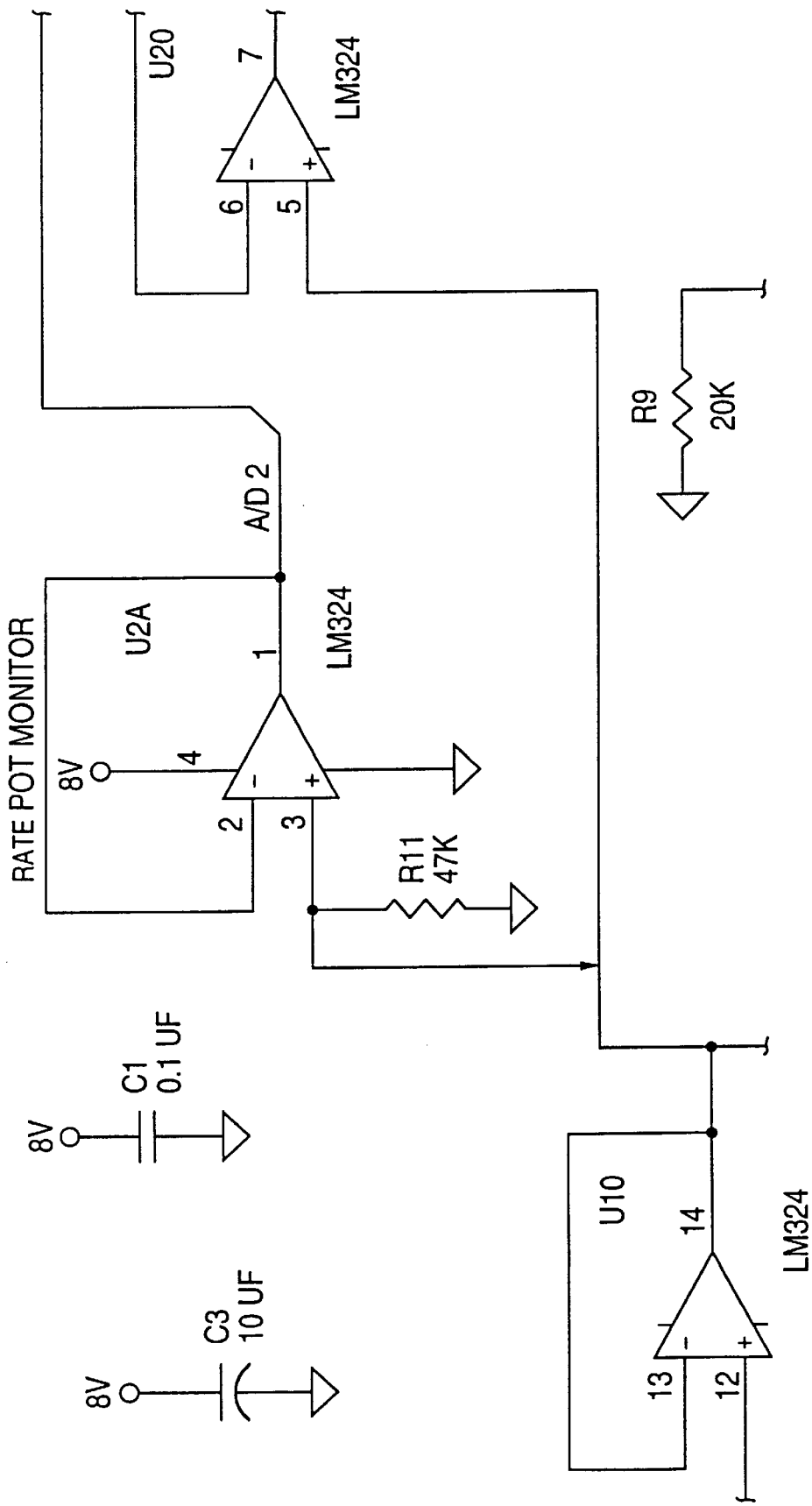
Figure 15D:
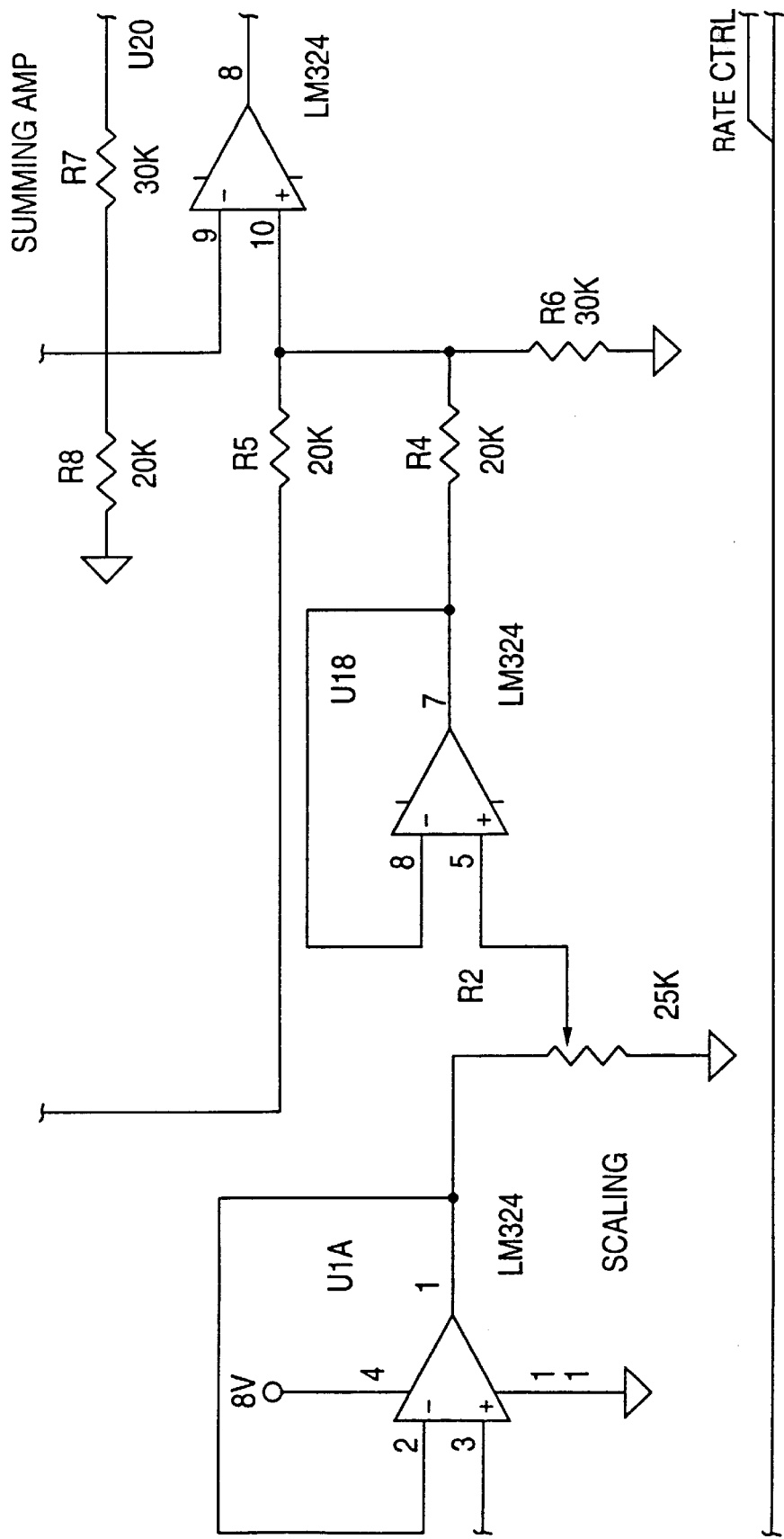
Figure 15E:
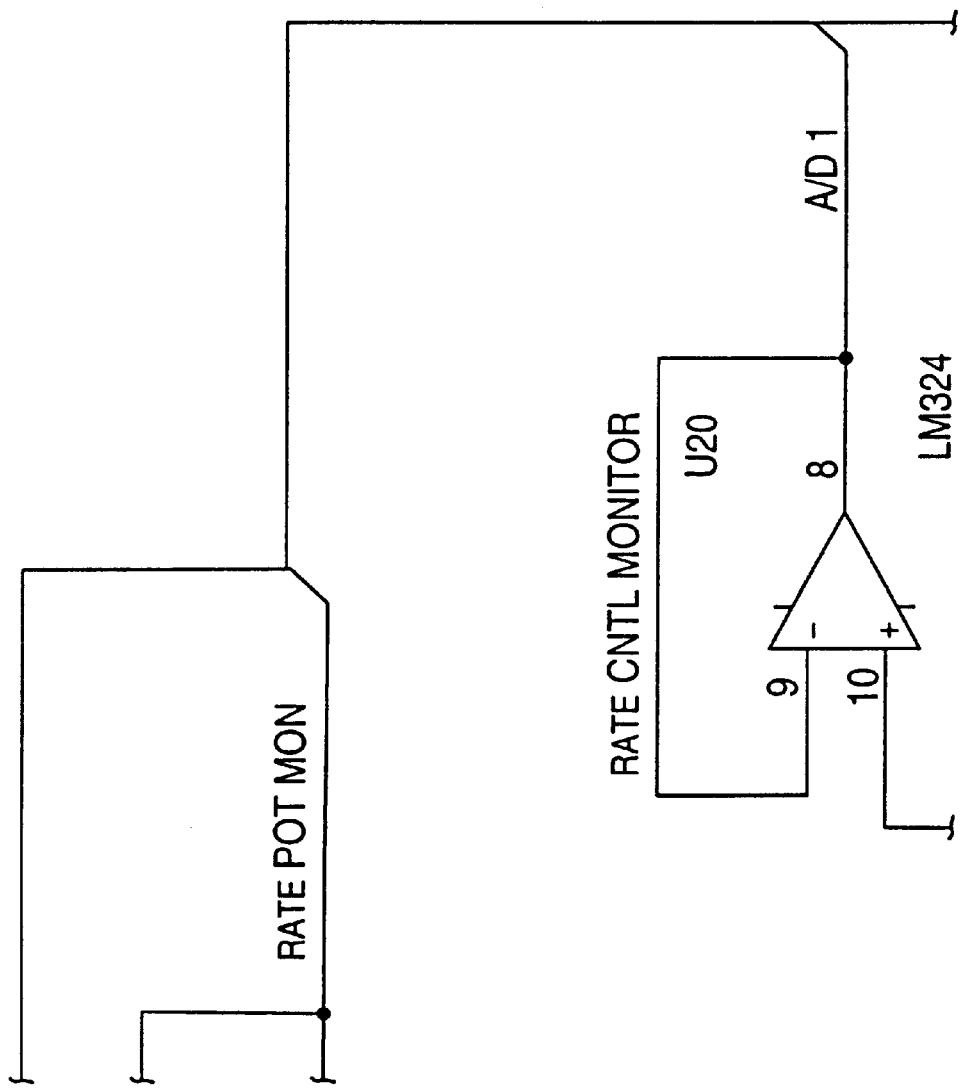
Figure 15F:
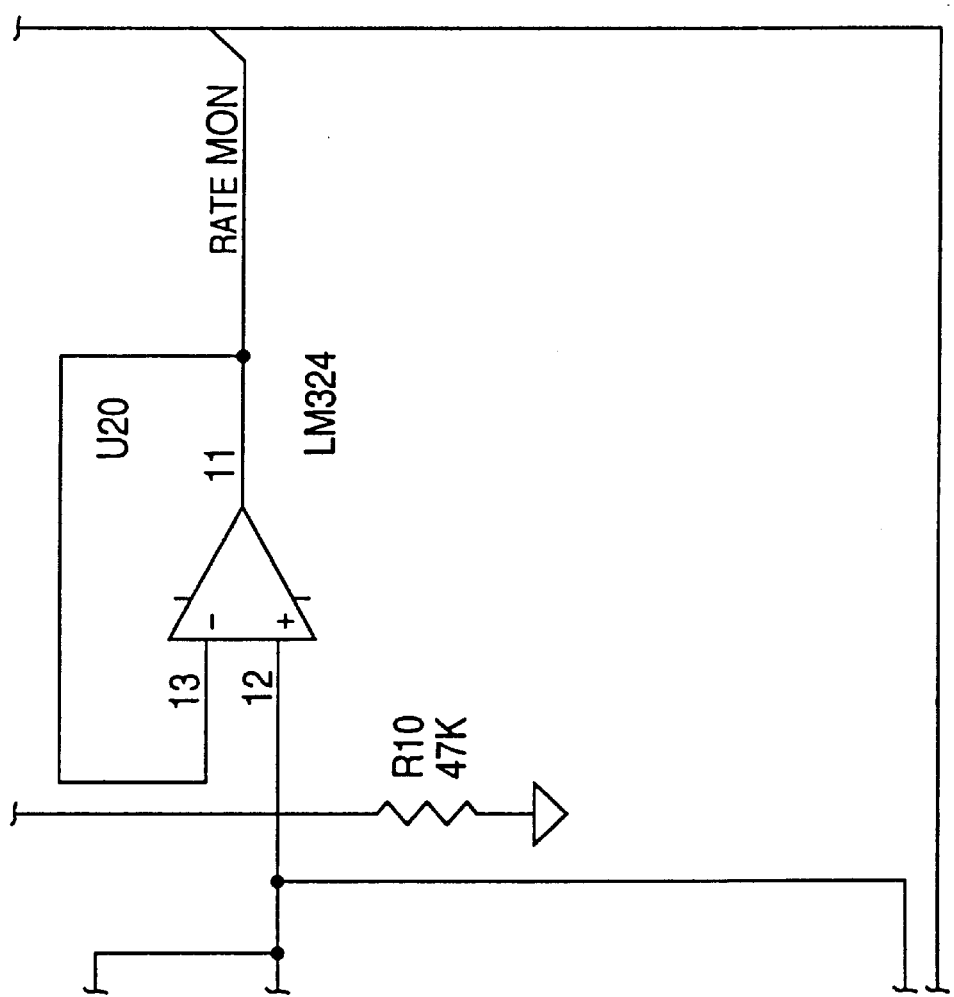
Figure 16:
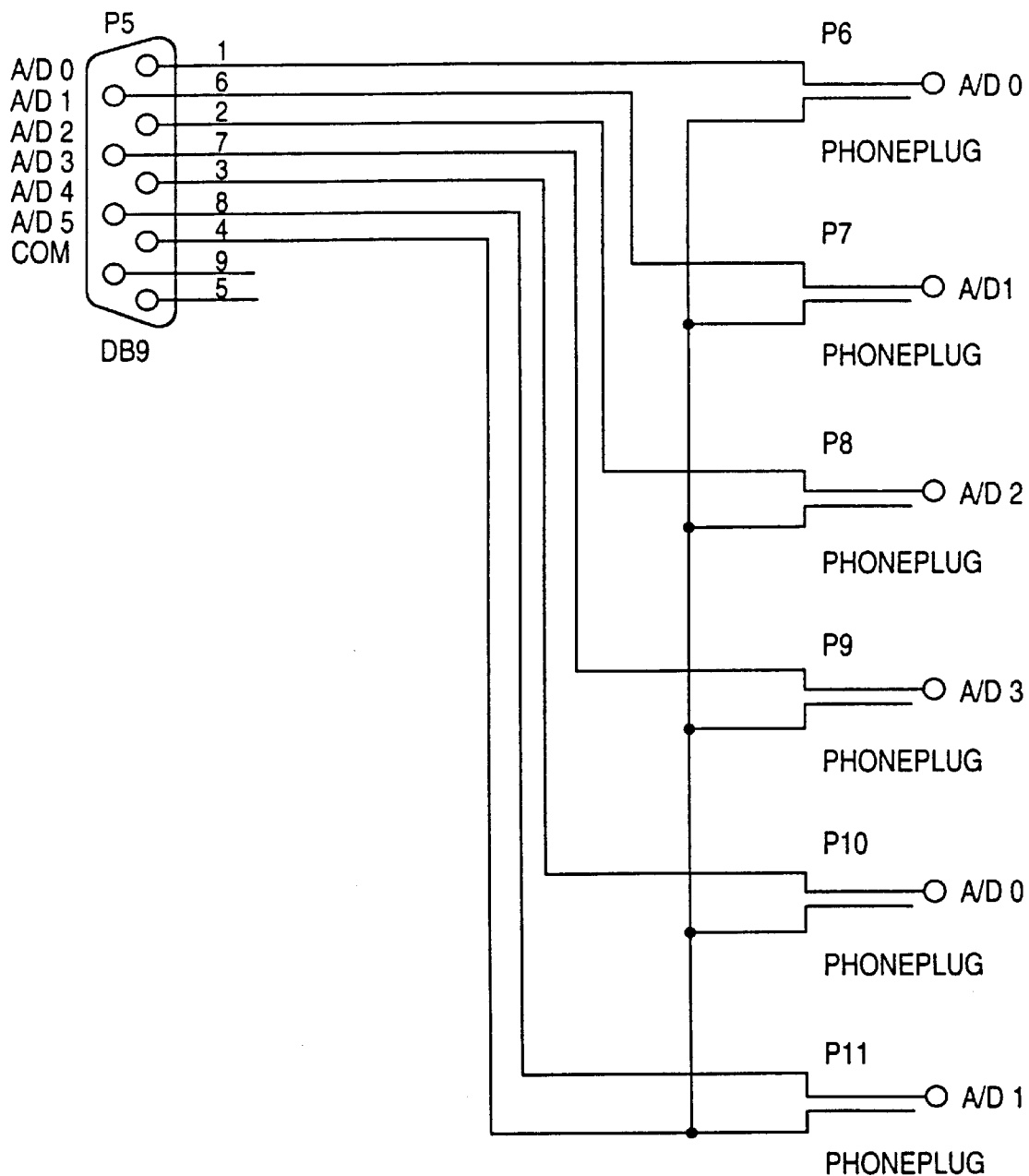
FIGS. 16 and 17 document (FIG. 6) the cable used to interface the Ohio Modulation Unit to the 'DAS16 Jumper Box' (FIG. 7), which is connected to the 37 pin connector on the Metrabyte DASH16 A/D and D/A converter.
Figure 17:
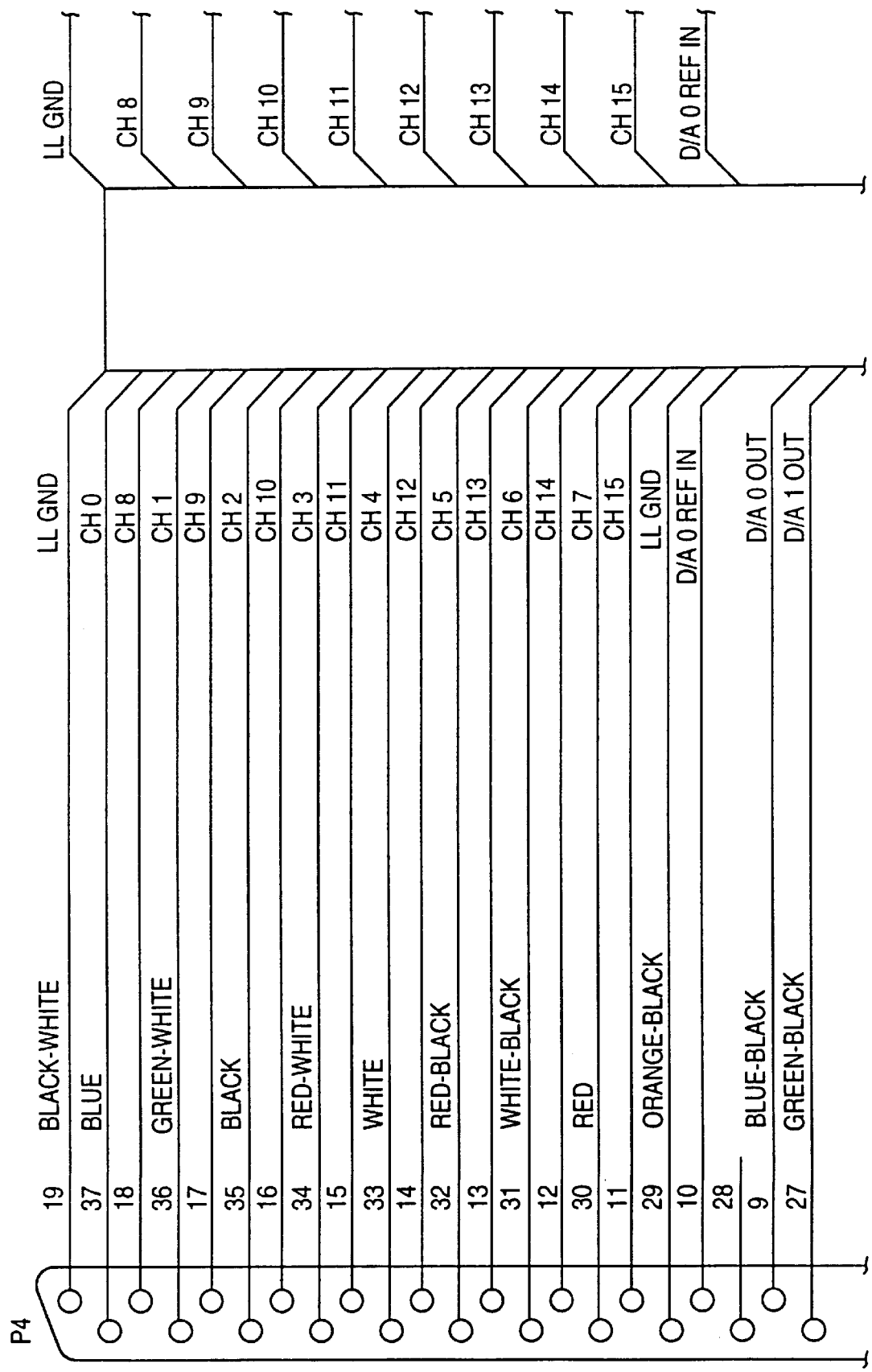
Figure 17B:
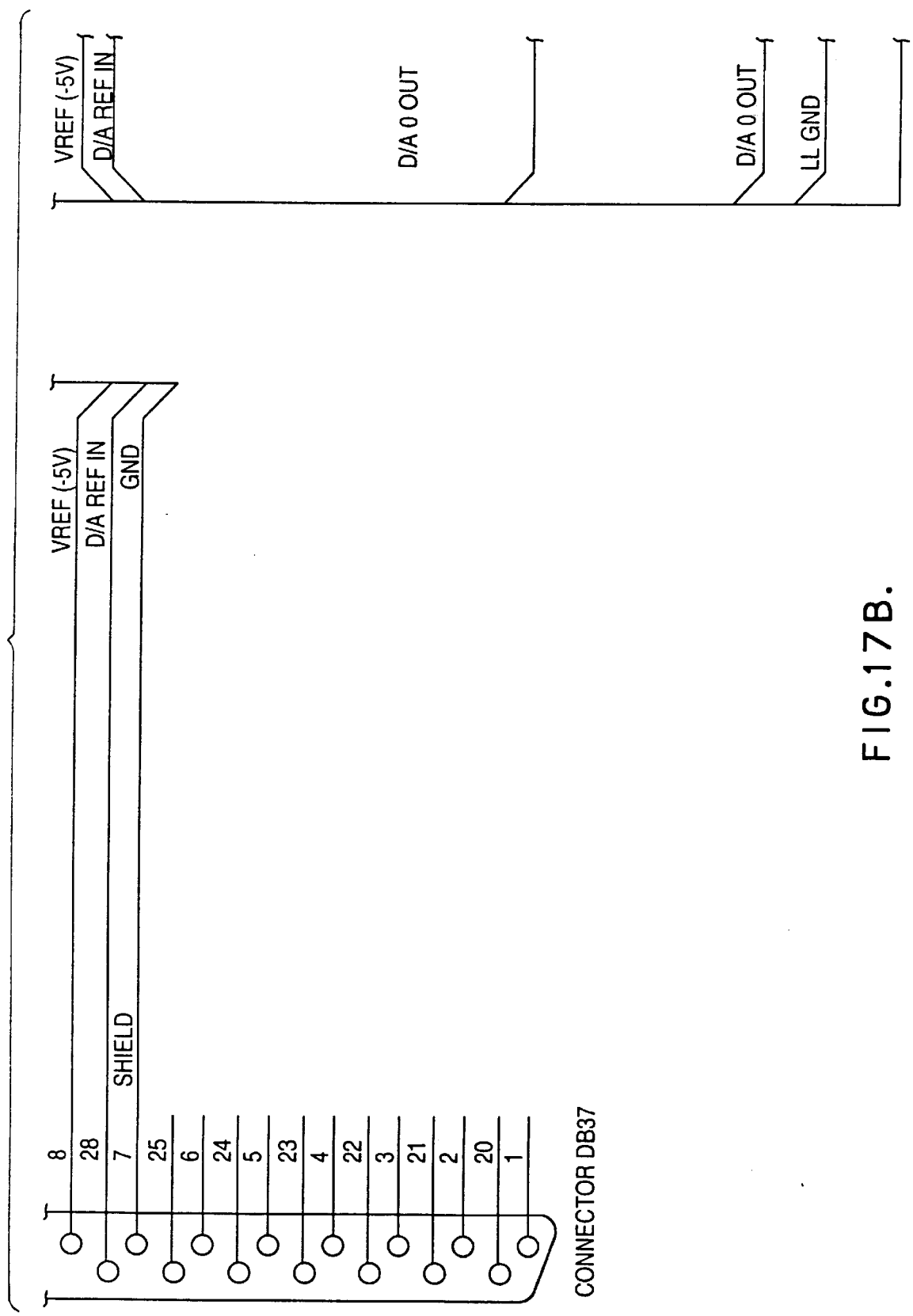
Figure 17C:
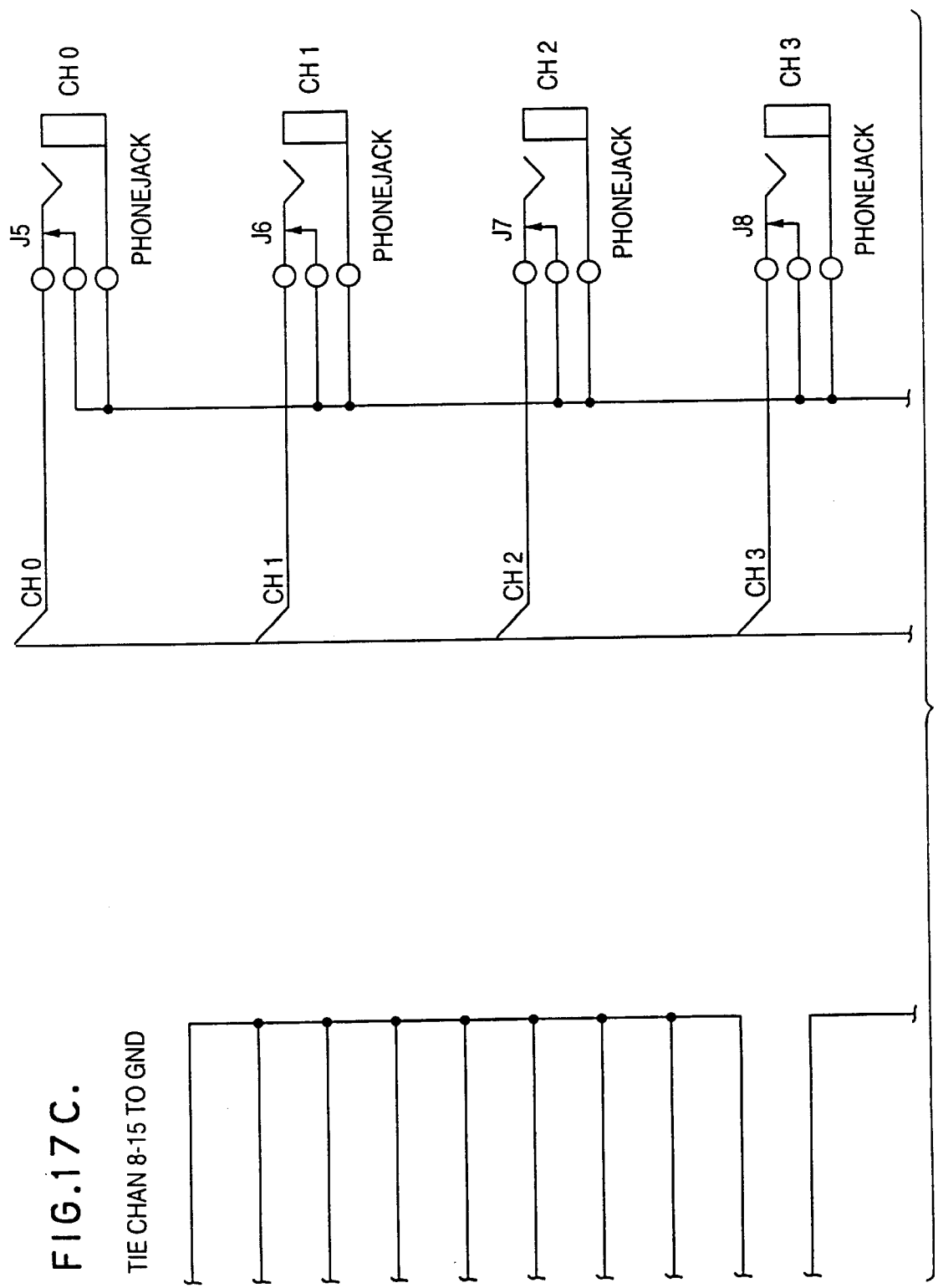
Figure 17D:
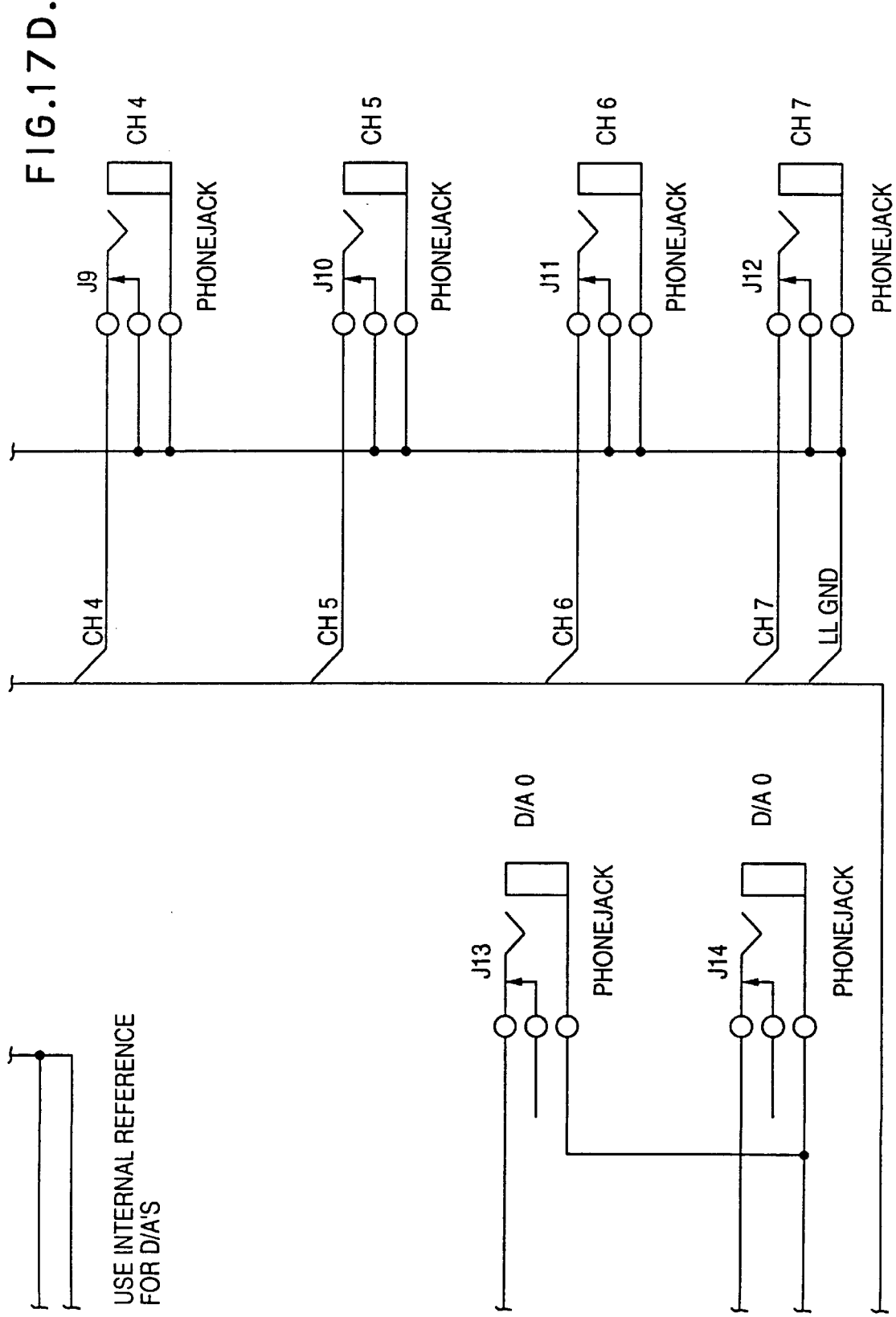

Computer-controlled Ventilation: The ventilation used in this experiment was an Ohio 7000 having electronics as illustrated in FIGS. 11 to 17 described above. The computer-controller software (Table 8) allows the rate and volume settings of the ventilator controls to be modulated independently via a previously generated data file. Data from this modulation file is depicted graphically in FIG. 9. A frequency vs respiratory rate plot is shown in FIG. 10. The modulation file was generated from hemodynamic and respiratory excursions from an anesthetized dog. This information was captured by data acquisition, processed and scaled to produce breath-to-breath. variability. Ventilatory variability can also be measured directly, stored and subsequently used to control the ventilation. Hardware was also developed to implement computer-control of the ventilator which necessitated converting voltage outputs from the breath-to-breath variability period to control ventilator respiratory rate and tidal volume, as seen in FIGS. 11 to 17. In this experimental configuration, only RR was changed. As there was employed a ventilator which functioned as a volume divider, change in the RR resulted in reciprocal changes in the TV. Functions were developed to convert ventilator rate and volume into voltage and vice versa. Output to control RR was updated every 400 msec and changed accordingly based on the modulation data file. The computer ventilator RR was set to 10 breaths/min baseline and the modulation file programmed ventilation from 10 to 22 breaths/min with a mean value of 15 breaths/min.

Post-hoc analysis: The data file of airway pressures was processed to integrate the area under the pressure time curve to give mean airway pressure. Mean peak airway pressure was also calculated. Because of the variability in RR and TV in the computer-controlled ventilator group, a minimum of 25 breaths were analyzed in each experiment. At the end of each experiment, the animal was killed with a lethal dose of thiopental, and a sternotomy done to remove the lungs. The lungs were weighed wet and then suspended and aerated to commence drying. The following day, the lungs were placed in an oven to dry to a stable weight (±5 percent on consecutive days). The wet:dry lung weight ratio was calculated.

Statistical Analysis: Multiple comparisons of data within and between groups was with repeated measures ANOVA. A p-value $\leq 0.05$ was considered significant for group x time interactions or differences between groups. Least squares means test matrices were generated for post-hoc comparisons. Bonferroni's correction was applied when multiple comparisons were examined within groups. Single comparisons between groups were by Student's t-test, p $\leq 0.05$ considered significant.

Example 2

This Example provides the results of the experimentation described in Example 1.

The computer-controlled ventilator varied respiration from 10 to 22 breaths/min (mean ±SD; 15.0±2.3). There were 369 RR and TV combinations over 1089 sec before the modulation file looped to repeat itself.

The demographic data from the experiments is shown in Table 3 below. There were 7 animals in the computer group and 6 in the control ventilator group. The animals in the two groups did not differ for weight or in the amount of oleic acid infused to induce the lung injury. The mean airway pressure did not differ between groups nor did the mean peak airway pressure. There was no difference between groups in the wet:dry lung weight ratio.

There was no difference between groups for blood or nasopharyngeal temperature (group x time interaction; p =0.1772 and 0.2665 respectively) (Table 4 below). A group effect was seen for baseline blood temperature of 0.6 degrees. In both groups, temperature increased significantly following lung injury. A marked difference was seen between groups for hemoglobin concentration (p =0.0014 group x time interaction). In both groups hemoglobin increased significantly following lung injury, but continued to increase in the control group. There was no interaction for pH between groups (p=0.2325) but there was a group effect with lower pH in the latter periods of the experiment in the control group.

Hemodynamic data is shown in Table 5 below. The MAP was stable between groups (group x time interaction; p=0.4429). In both groups MAP decreased significantly following lung injury. The MPAP showed an interaction (p =0.0198). In both groups the MPAP increased markedly following oleic acid. Baseline MPAP was significantly higher in the computer group then lower by 90 minutes. The PCWP was essentially identical between groups. No interaction was seen for PVR but a marked group effect was seen (p=0.0001). In both groups PVR increased dramatically with lung injury. The PVR was significantly higher from 90 min on in the control group. There was no difference between groups for cardiac output at any time period. In both, the CO decreased to about 60 percent of control and remained unchanged.

Respiratory gas data is shown in Table 6 below. End-expired $CO_2$ ($PeCO_2$) did not differ between groups. There was a significant increase in $PaCO_2$ following lung injury in both groups. This correlated to the significant increase in dead space ventilation (VD/VT) seen. Importantly, a significant group x time interaction was seen for $PaO_2$ (p=0.0448). A markedly significant group effect was seen as well (p=0.0001). This is evident from significantly greater $PaO_2$ at time periods 60–150 min after oleic acid infusion. Of note, at baseline and at Time 0, $PaO_2$ values are not significantly different. In both groups the shunt fraction (QS/QT) increased significantly following lung injury.

Example 3

This Example discusses the results obtained in the experiments described in the preceding Examples.

In these experiments described in Example 2, it has been demonstrated that oxygenation is improved by modifying mechanical ventilation to incorporate biologic variability. Through use of a computer-controller, variability in RR and TV resulted in significantly improved $PaO_2$ compared to standard IPPV with the same ventilator. This improvement in oxygenation was accomplished without an increase in mean airway or mean peak airway pressures.

No differences were seen between the two groups for amount of oleic acid administered to injure the lungs. The wet:dry lung weight ratios suggest a similar injury between the two groups. The two groups were very similar at baseline and following lung injury for PCWP, CO and PVR. Similar increases in shunt fraction and dead space ventilation were also seen for these two groups over the same time periods. Thus, the two groups appear not to differ prior to being randomized to control or computer-controlled ventilation.

Figure 8:
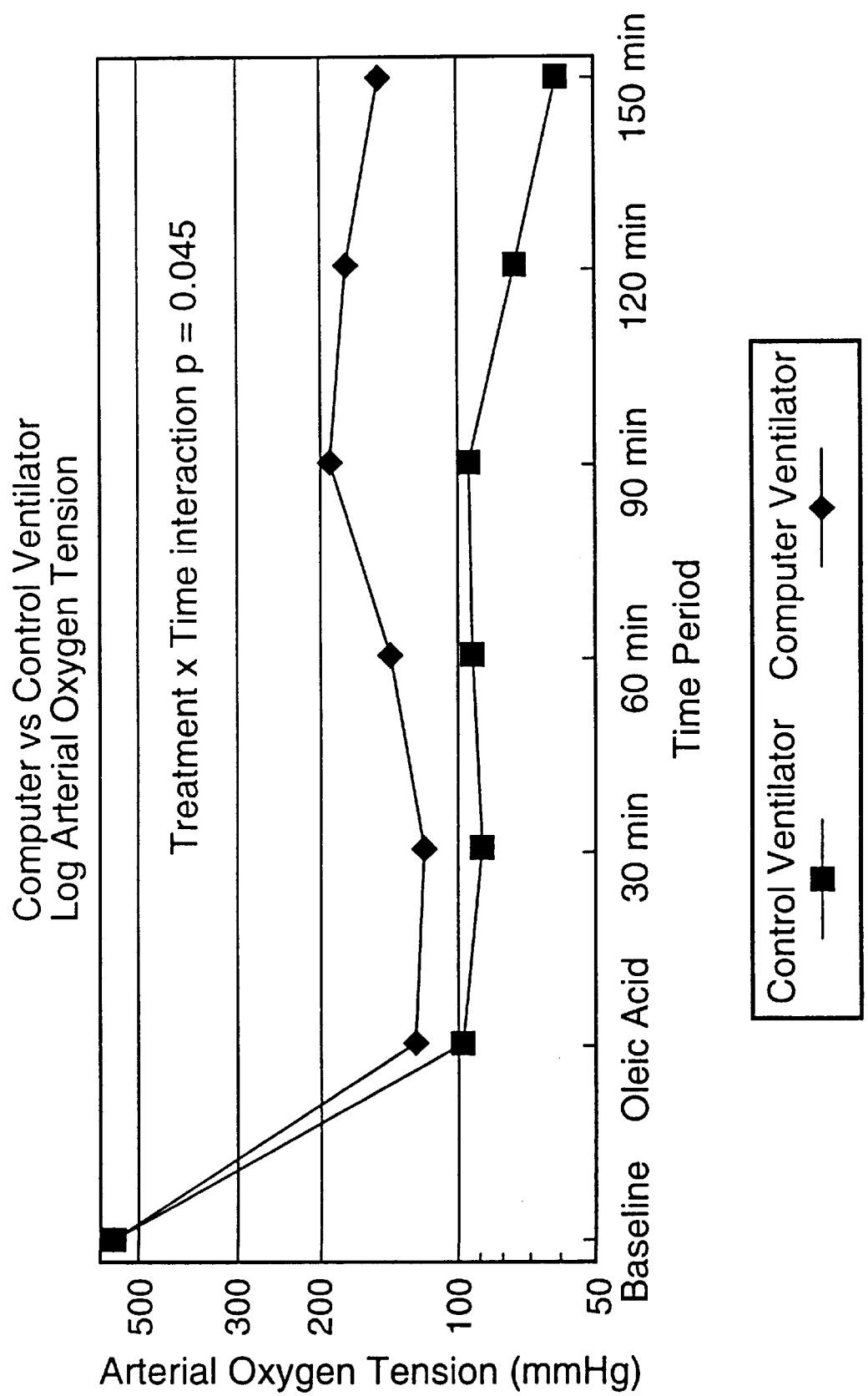
FIG. 8 shows a comparison of arterial oxygenation ($PaO_2$ in mm Hg) for computer-controlled vs. conventional mechanical ventilation in a porcine oleic acid lung injury model. Significantly greater $PaO_2$ is seen at the latter time periods in the experiment in animals ventilated with the computer-controlled ventilator (operation in accordance with the invention).

As configured for this study, the ventilator delivered 369 different RR and TV combinations with a mean RR of 15 breaths/min over 1089 sec (18.2 min). This is contrasted to a single RR of 15 breaths/min throughout the duration of the experiment in the control group. Some variability exists in the control group because MV was adjusted to attempt to maintain $PaCO_2 \leq$ mm Hg when VD/VT increased with lung injury. However, this entailed only a maximum of 6 changes in MV, over the course of any one experiment, when MV was changed if $PaCO_2$ was out-of-range, at the end of any 30 min measurement period. Thus, over a 30 min measurement period, RR and TV were essentially fixed in the control group but there were 369 x30/18.2=608 different RR and TV combinations in the computer group. If, as Suki et al. (Nature, Vol. 368, April 1994, p. 615–618) suggest, airway recruitment is stochastic, then the probability of airway opening is dramatically improved using the computer-controlled ventilator. The experimental results provided herein indirectly suggest that this finding is so. Of greatest significance is that mean $PaO_2$ improved following lung injury in the computer group out to 150 min (FIG. 8) compared to an inexorable decline in $PaO_2$ in the control group. This improved $PaO_2$ was associated with significantly lower MPAP and PVR at identical PCWP in the computer group suggesting better ventilation/perfusion matching and lower pulmonary vascular resistance at similar cardiac outputs. The marked difference in hemoglobin concentration following lung injury is an independent marker that the two ventilatory modes differ. The increasing hemoglobin concentration in the control group suggests further accumulation of lung water. In the computer group, hemoglobin concentration remained essentially stable. This is especially so as the initial mean increase in hemoglobin concentration is identical in the two groups (26 percent). At Time 0, both groups were control mode ventilated. Only after Time 0, was computer ventilation initiated. Therefore, by inference, during the conduct of the experiment, lung water accumulation was less in the computer group with associated better oxygenation.

Example 4

This Example illustrates the materials and methods used to evaluate a CPB pump in dogs, using the computer control operation described above with reference to FIGS. 1 to 4.

Experimental Preparation: Twelve mongrel dogs (21±3 kg) were studied. All animals were anesthetized with sodium thiopental (25 mg.kg$^{-1}$). The trachea was intubated and the animal ventilated with $O_2$. The minute ventilation was adjusted to maintain $PaCO_2$ at 35 to 40 mm Hg. The dog was positioned in a stereotactic head-frame in a modified sphinx position. Bipolar EEG electrodes were placed over the parietal hemisphere bilaterally and monitored by an Interspec Neurotrac® in raw EEG mode. Temperature was measured in the nasopharynx using a calibrated YSI telethermometer®. Anesthesia was maintained with isoflurane 1.3% end-tidal (1 MAC) during the surgical preparation. Following thoracotomy, the isoflurane was discontinued for a minimum of 30 min and the EEG made isoelectric with a bolus of thiopental. A continuous infusion of thiopental was initiated at 10 mg.kg$^{-1}$.hr$^{-1}$ to maintain the EEG isoelectric during CPB. Neuromuscular relaxation was achieved with pancuronium bromide.

A flow-directed catheter was advanced through the left femoral vein into the right atrium for central venous pressure (CVP) monitoring. A femoral artery catheter was advanced into the distal aorta for arterial pressure (MAP) monitoring. A double lumen (7.5 FR) catheter was inserted into the left brachial artery for intermittent blood withdrawal. The superior sagittal sinus (SSS) was exposed by trephine and the posterior one-third was cannulated non-occlusively by insertion of a 22-gauge intravenous catheter. Continuous cerebrospinal fluid pressure (CSFP) measurements were recorded by inserting a 22-gauge spinal needle into the cisterna magna with the use of a micromanipulator (Narishige®). A right thoracotomy was performed. The right atrium and proximal aorta were cannulated with a single stage 38 Fr atrial and Jostra®21 Fr or 24 Fr aortic cannula, respectively. Following the initiation of CPB, the left ventricle was vented by a cannula inserted through the right superior pulmonary vein and the proximal aorta was occluded with a Seldinger vascular clamp.

All blood pressures and the CSFP were measured by calibrated Abbott® transducers referenced to the intra-auricular line. Data were recorded continuously on paper by an oscillograph (recorder model 7754A®, Hewlett Packard) and intermittently on hard disk by an IBM PC-AT® computer based data acquisition system (Dataq Instruments®). The latter data are reported. Arterial and SSS blood gases were measured before and after each microsphere injection by an ABL-3 Acid-Base Laboratory (Radiometer®) at 37° C. and not corrected for temperature. Arterial and cerebral venous (SSS) oxygen content and hemoglobin were measured by Radiometer OSM-3 (specific for canine blood).

Cardiopulmonary bypass was conducted utilizing a Travenol® non-pulsatile roller pump with a Terumo Capiox E membrane oxygenator and a Bentley® arterial line filter (25 $\mu$m). The roller pump and oxygenator were primed with 2.5 to 3.01 of lactated Ringer's and 1 to 2 units (500 to 1000 ml) of canine whole blood in CPDA-1 solution. The blood was obtained 48 to 72 hours prior to the experiment from a donor animal and refrigerated at 4° C. The animal was systemically heparinized with 300–400 IU•kg$^{-1}$ of heparin (Organon: porcine intestine®) and additional doses as required, to give an activated clotting time (ACT) $\geq$400 sec (Hemochron 400®). Throughout the experiment the animal had an intravenous infusion of lactated Ringer's at 200–250 ml.hr$^{-1}$ containing 25 mEq.1$^{-1}$ of $NaHCO_3$. This was done to maintain a stable hemoglobin concentration and acid-base state during the experiment ($\alpha$-stat acid-base management). Norepinephrine (40 $\mu$g) was injected into the oxygenator coincident with initiating CPB to minimize the hemodynamic consequences. The animals were randomized to one of two groups: non-pulsatile bypass group; Group NP (n=6), or computer-controlled bypass group; Group CP.

Group CP (n=6). Following the initiation of CPB, cooling to 28° C. commenced immediately in both groups. Temperature was altered using a Travenol heat exchanger. In both groups of animals, the mean cerebral perfusion pressure (CPP; MAP—mean CSFP) was maintained at greater than 60 mm Hg. Hypothermic non-pulsatile CPB continued for 105 min in Group NP and for 15 min in Group CP while the computer-control was being established (see below) and then for 90 minutes with computer pulsation. At 105 min, rewarming was commenced. In both groups, rewarming to baseline temperature was over 30 min. At 45 min after the start of rewarming, cerebral blood flow (CBF) and blood gas samples were obtained.

In these experiments, for each animal in Group CP, by means of a data acquisition system, a 15 min data file of blood pressure was obtained following induction of anesthesia. Data from a typical modulation file is depicted graphically in FIG. 2. A typical output from the computer-controller roller pump relating computer voltage output and the changes in MAP are shown in FIG. 3. The data is processed by a computer programmed using Table 1.

Cerebral Blood Flow Measuremnts: The radioactive microspheres, ultrasonicated in saline, were injected into the arterial cannula, approximately 1 meter proximal to the aortic root, after the $PaCO_2$ was stable between 35–40 mm Hg. If the $PaCO_2$ could not be stabilized in this range by adjusting the $O_2$ flow to the oxygenator, $CO_2$ was added with a Sechrist® mixer. Approximately 2.5×10$^6$ microspheres (15 $\mu$m diameter) were injected into the arterial cannula. This number of microspheres assured greater than 400 microspheres/sample for accurate blood flow measurement (Heymann et al., 1977). The randomly selected microspheres were labelled with $^{46}$Sc, $^{85}$Sr, $^{141}$Ce, $^{95}$Nb, or $^{113}$Sn (New England Nuclear). A Harvard pump® withdrew a reference blood sample for determination of organ blood flow (25 ml) from the brachial artery (Compugamma®) after being weighed. The counts/min were converted to regional CBF in ml.g$^{-1}$ .min$^{-1}$ with the use of standard equations.

Total CBF (tCBF) was determined by summing weighted flows to all brain regions and dividing by total brain weight. Similarly, cerebral hemispheric CBF (hCBF) and brain stem CBF (bsCBF) were determined by the summation of weighted flows to the cerebral hemispheres and brain stem, respectively. The CPP was measured as (MAP—mean CSFP) and cerebral metabolic rate for $O_2$ ($CMRO_2$) as hCBF X (Art—SSS $O_2$ content) in ml $O_2$.g$^{-1}$ .min$^{-1}$.

Statistical Analyses: Changes over time for blood gas and hemodynamic variables were evaluated by analysis of variance (ANOVA) for repeated measures. When ANOVA was significant, comparisons were made with the least-squares means test. Data are presented as mean ±SD.

Example 5

This Example describes the results obtained using the materials and methods described in Example 4.

Temperatures and hemodynamic data are shown in Table 7 below. The temperature did not differ between groups for either the period of hypothermia or following rewarming. In all instances, the nasopharyngeal temperature was able to be increased to 35° C. within the 30 min time frame without exceeding a temperature gradient of 8° C. between the heat exchanger and the nasopharyngeal measurement sites. The MAP remained stable over the two temperatures in both groups. A difference in MAP was seen between groups with MAP being greater at both temperatures in Group CP but there was no group x time interaction (p=0.0904). In both groups the CSFP increased with rewarming. The CPP was stable over time, within groups, with no group x time interaction (p=0.771).

The blood gas and blood $O_2$ content data are shown in Table 8 below. Both groups had similar hemoglobin concentrations during CPB and similar pH and $PaCO_2$. A significant group by time interaction was observed for SSS $O_2$ content (p=0.0005), SSS $O_2$ (p=0.003), and art-SSS $O_2$ content difference (p=0.011). In all instances Group CP remained more stable. In Group NP, there was a significant decrease in SSS $O_2$ content and SSS $O_2$ with rewarming, and an increase in the art-SSS $O_2$ content difference.

The regional CBF and $CMRO_2$ data are shown in Table 8. In both groups regional CBF increased with rewarming. There was no difference between groups for CBF in any region. Flow:metabolic coupling decreased with rewarming in Group NP. There was no difference in $CMRO_2$ between groups. In both groups $CMRO_2$ increased with rewarming.

Example 6

This Example discusses the results obtained in Example 5.

Figure 7:
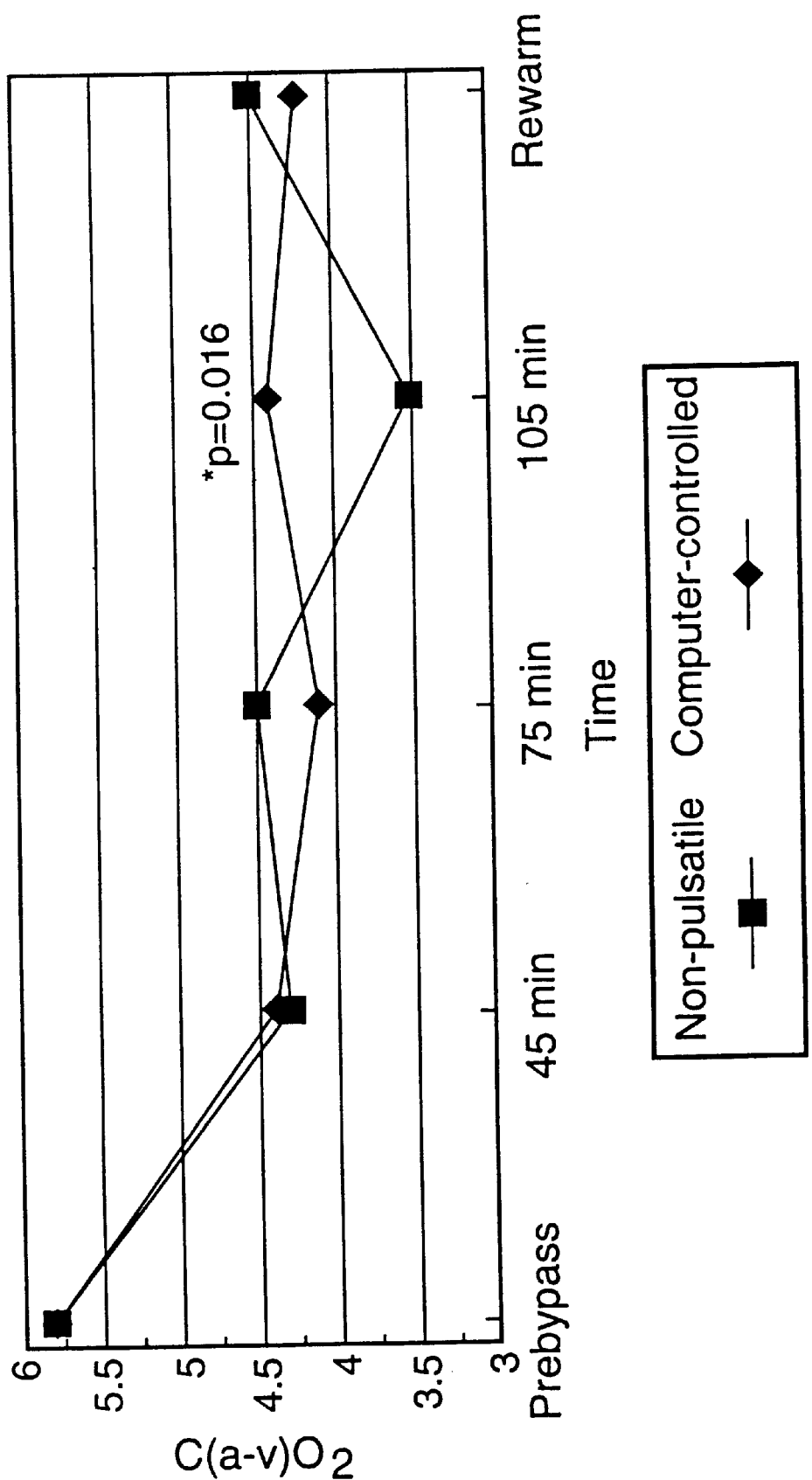
FIG. 7 shows the arterial minus superior sagittal sinus (cerebral venous) oxygen content difference during CPB with computer-controlled and conventional roller pump bypass in dogs (n=6 both groups). The oxygen content difference is stable during conduct of CPB in the computer-controlled group (operation in accordance with the invention). In the control group (conventional roller pump), increased oxygen extraction occurs during the period of rewarming compared to the hypothermic period of CPB immediately before. Such changes in oxygen content difference with rewarming are associated with cognitive impairment following CPB in man.

Use of computer-controlled CPB roller pump according to the invention, which restores inherent biologic variability, as described in Examples 4 and 5, prevents cerebral deoxygenation during rewarming. The SSS $O_2$, SSS $O_2$ content, and the art-SSS $O_2$ content difference were all stable following rewarming in Group CP. In contrast, in Group NP, the SSS $O_2$ and SSS $O_2$ content decreased and the art-SSS $O_2$ content difference increased with rewarming suggesting cerebral deoxygenation with conventional non-pulsatile CPB (Table 8, FIG. 7). This experimental group had CPB managed similarly to that of patients in a study by Croughwell et al. (Ann. Thorac. Surg. 1994; 58:1702–1708) (α-stat acid-base management, use of arterial line filter and membrane oxygenator, and a similar duration of CPB). In all instances, the cerebral deoxygenation was not as severe as that seen by Croughwell et al. However, the changes seen were similar to those in the clinical scenario, and the more important observation is that computer-controlled CPB prevented these changes with rewarming.

The differences between the two groups does not appear to be a consequence of changes in CBF with computer-controlled CPB. It is of interest that the $O_2$ content difference was lower during hypothermia in Group NP than in Group CP and became greater with rewarming. This may suggest that there was a difference in distribution of CBF during CPB between the two groups given no difference in tCBF. If so, this finding could imply two flow pathways with CPB (a shunt and a parenchymal flow pathway). The use of computer-controlled CPB which restored inherent biologic rhythms would appear to provide better parenchymal flow, resulting in a greater oxygen content difference during the hypothermic bypass period and an ability for recruitment of the capillary bed in proportion to the requirements of increased metabolic demand with rewarming. With non-pulsatile bypass, the lower $O_2$ content difference at similar tCBF suggests a greater shunt flow, during the period of hypothermia. With rewarming, parenchymal blood flow appears inadequate to meet the increased metabolic demands of the tissue which results in increased extraction of oxygen and an increased $O_2$ content difference, lowered SSS $O_2$ and $O_2$ saturation. These results suggest that the greater deoxygenation seen with conventional CPB may be a consequence of capillary closure to parenchymal beds due to non-pulsatile bypass.

Non-pulsatile perfusion has been demonstrated to increase tissue water and alter vascular properties in other tissues such as the lung. These effects of the abnormal pulsation are unaltered by hypothermia, anesthesia or use of arterial filters. Hence these presumed neural protective interventions may not be helpful and may account for lack of clinical correlates of improved neurologic outcome with their institution. The improvements seen with computer-controlled pulsatile flow provides strong indirect evidence that the microembolic theory inadequately explains why the brain is damaged during CPB.

The better cerebral oxygenation occurring with computer-controlled CPB is not likely due to any change in the microembolic load presented to the brain. Pulsation, per se, should not alter the microembolic load, and the CBF was identical in the two groups, at both temperatures suggesting another mechanism independent of microemboli being the causative reason for the difference between groups. Microemboli are felt to be the leading candidates to explain the neurologic and neuropsychologic damage following CPB. The microemboli theory cannot effectively explain the reason for the increased $O_2$ extraction seen on rewarming. An explanation of parallel flow pathways during CPB (one shunt pathway and one parenchymal flow pathway) which is a consequence of the monotonous regular non-pulsatile blood flow with resultant cerebral capillary bed closure can explain why neural damage occurs despite strategies to decrease cerebral blood flow and thereby decrease the embolic load to the brain. Computer-controlled pulsation creates a more physiologic flow state with improved cerebral oxygenation following rewarming.

SUMMARY OF DISCLOSURE

In summary of this disclosure, the present invention provides computer control of the operation of a cardiopulmonary bypass pump, a lung ventilator or other device which provides simulation of in vivo variability of flow of a biologic fluid to an organ. Modifications are possible within the scope of this invention.

TABLE 3

| Variable | Control Ventilator | Computer Ventilator | p-value |
|---|---|---|---|
| Weight (kg) | 21.7 ± 2.8 | 23.4 ± 1.3 | ns |
| Oleic Acid Infused (ml/kg) | 0.20 ± 0.05 | 0.24 ± 0.11 | ns |

TABLE 3-continued

| Variable | Control Ventilator | Computer Ventilator | p-value |
|---|---|---|---|
| Mean Airway Pressure (cm H$_2$O) | 12.02 ± 0.54 | 11.41 ± 0.39 | ns |
| Mean Peak Airway Pressure (cm H$_2$O) | 59.5 ± 1.3 | 56.6 ± 3.0 | ns |
| Wet:Dry Weight Ratio | 10.1 ± 1.1 | 9.2 ± 1.2 | ns |

Mean ± S.D.
Control Group n = 6
Computer Group n = 7 except for mean airway pressure and mean peak airway pressure
Control Group n = 4
Computer Group n = 3

TABLE 4

| | | Time (minutes) Following Oleic Acid Infusion | | | | | | |
|---|---|---|---|---|---|---|---|---|
| Variable | Baseline | 0 | 30 | 60 | 90 | 120 | 150 | 180 |
| Temp (° C.) | | | | | | | | |
| Computer | 37.8 ± 1.0 | 38.3 ± 1.0* | 38.4 ± 1.1* | 38.5 ± 1.0* | 38.4 ± 0.9* | 38.5 ± 1.0* | 38.6 ± 1.1* | 38.6 ± 1.3* |
| Control | 37.2 ± 1.2+ | 38.0 ± 1.2* | 38.3 ± 1.1* | 38.4 ± 1.2* | 38.5 ± 1.0* | 38.5 ± 1.4* | 38.9 ± 1.2* | 39.0 ± 1.3* |
| Temp (° C.) | | | | | | | | |
| Computer | 36.8 ± 0.6 | 37.0 ± 0.9 | 37.3 ± 0.6 | 37.1 ± 0.8 | 37.3 ± 0.5 | 37.2 ± 0.5 | 37.2 ± 0.7 | 37.2 ± 1.1 |
| Control | 36.4 ± 1.2 | 37.1 ± 1.1* | 37.5 ± 0.9* | 37.3 ± 0.7* | 37.4 ± 0.8* | 37.7 ± 0.7* | 37.7 ± 1.0* | 37.9 ± 1.0* |
| Hgb (g %) | | | | | | | | |
| Computer | 9.2 ± 1.0 | 11.6 ± 1* | 11.8 ± .8* | 11.9 ± .7* | 11.6 ± .7* | 11.7 ± .5* | 11.8 ± .8* | 12.3 ± .7* |
| Control | 10.0 ± .9+ | 12.6 ± 1*+ | 13.0 ± 1*+ | 13.3 ± 1.3* | 13.7 ± 1*+ | 13.9 ± 1*+ | 14.1 ± 1*+ | 14.5 ± .8*+ |
| pH | | | | | | | | |
| Computer | 7.49 ± .03 | 7.37 ± .04* | 7.38 ± .05* | 7.36 ± .07* | 7.36 ± .06*+ | 7.37 ± .04*+ | 7.37 ± .04*+ | 7.34 ± .05*+ |
| Control | 7.48 ± .04 | 7.38 ± .03* | 7.35 ± .02* | 7.33 ± .02* | 7.33 ± .03* | 7.33 ± .03* | 7.31 ± .06* | 7.29 ± .07* |

Mean ± S.D.
*P < 0.05 within Groups
+P < 0.05 between Groups
Bonferroni's correction applied for multiple comparisons
Computer Group n = 7
Control Group n = 6
Temp = blood temperature
Temp = nasopharyngeal temperature

TABLE 5

| | | Time (minutes) Following Oleic Acid Infusion | | | | | | |
|---|---|---|---|---|---|---|---|---|
| Variable | Baseline | 0 | 30 | 60 | 90 | 120 | 150 | 180 |
| MAP (mm Hg) | | | | | | | | |
| Computer | 91 ± 15 | 78 ± 11*+ | 75 ± 14* | 75 ± 12* | 73 ± 10* | 75 ± 12* | 76 ± 9* | 77 ± 8* |
| Control | 92 ± 14 | 68 ± 16* | 69 ± 20* | 71 ± 14* | 71 ± 15* | 78 ± 19* | 79 ± 20* | 78 ± 17* |
| MPAP (mm Hg) | | | | | | | | |
| Computer | 22 ± 5 | 40 ± 4* | 39 ± 3* | 39 ± 5* | 37 ± 5* | 39 ± 6* | 40 ± 7* | 42 ± 4* |
| Control | 19 ± 2+ | 37 ± 4* | 37 ± 6* | 40 ± 5* | 40 ± 3*+ | 40 ± 5* | 43 ± 2* | 43 ± 3* |
| PCWP (m Hg) | | | | | | | | |
| Computer | 10 ± 1 | 11 ± 1 | 11 ± .6 | 10 ± 1 | 10 ± .5 | 11 ± 1 | 12 ± 3 | 11 ± 3 |
| Control | 11 ± 1 | 12 ± 1 | 11 ± 2 | 11 ± 1 | 11 ± .8 | 10 ± 1 | 10 ± 2+ | 10 ± 1 |

TABLE 5-continued

| Variable | Baseline | Time (minutes) Following Oleic Acid Infusion | | | | | | |
|---|---|---|---|---|---|---|---|---|
| | | 0 | 30 | 60 | 90 | 120 | 150 | 180 |
| PVR (mm Hg · $1^{-1}$ min) | | | | | | | | |
| Computer | 3 ± 1 | 12 ± 1* | 12 ± 2* | 12 ± 2* | 10 ± 2* | 12 ± 4* | 12 ± 5* | 11 ± 4* |
| Control | 2 ± .7 | 13 ± 4* | 13 ± 6* | 15 ± 6* | 14 ± 5*+ | 15 ± 5*+ | 15 ± 7*+ | 15 ± 5*+ |
| CO (1 · $min^{-1}$) | | | | | | | | |
| Computer | 4.2 ± .3 | 2.5 ± .4* | 2.6 ± .4* | 2.5 ± .4* | 2.6 ± .3* | 2.5 ± .3* | 2.5 ± .4* | 2.7 ± .4* |
| Control | 4.0 ± .9 | 2.4 ± .6* | 2.5 ± .9* | 2.5 ± .9* | 2.3 ± .6* | 2.5 ± .8* | 2.5 ± 1.0* | 2.5 ± .8* |

Mean ± S.D.
*P < 0.05 within Groups
+P < 0.05 between Groups
Bonferroni's correction applied for multiple comparisons
Computer Group n = 7
Control Group n = 6
MPAP = Mean Pulmonary Artery Pressure
PCWP = Pulmonary Capillary Wedge Pressure
PVR = Pulmonary Vascular Resistance
CO = Cardiac Output

TABLE 6

| Variable | Baseline | Time (minutes) Following Oleic Acid Infusion | | | | | | |
|---|---|---|---|---|---|---|---|---|
| | | 0 | 30 | 60 | 90 | 120 | 150 | 180 |
| $PeCO_2$ (mm Hg) | | | | | | | | |
| Computer | 17.5 ± 4.8 | 13.7 ± 2.6 | 14.4 ± 2.5 | 16.1 ± 3.2 | 14.7 ± 2.9 | 15.0 ± 2.2 | 13.1 ± 2.3 | 15.2 ± 2.7 |
| Control | 19.8 ± 3.7 | 16.1 ± 4.1 | 14.5 ± 2.5 | 15.4 ± 3.6 | 15.7 ± 3.8 | 16.8 ± 4.9 | 17.8 ± 6.8 | 17.3 ± 6.1 |
| $PaCO_2$ (mm Hg) | | | | | | | | |
| Computer | 36.3 ± 2 | 46.6 ± 3* | 45.3 ± 6* | 47.7 ± 8* | 45.8 ± 8* | 46.0 ± 4* | 46.8 ± 6* | 49.9 ± 6* |
| Control | 36.9 ± 2 | 43.6 ± 1* | 46.1 ± 4* | 48.2 ± 7* | 48.1 ± 3* | 49.0 ± 5* | 49.0 ± 7* | 51.2 ± 13* |
| $PaO_2$ (mm Hg) | | | | | | | | |
| Computer | 558 ± 31 | 133 ± 39* | 140 ± 68* | 155 ± 93* | 203 ± 88* | 197 ± 124* | 162 ± 119* | 116 ± 64* |
| Control | 556 ± 57 | 112 ± 56* | 103 ± 56* | 92 ± 51*+ | 90 ± 53*+ | 75 ± 20*+ | 65 ± 10*+ | 65 ± 15* |
| QS/QT | | | | | | | | |
| Computer | 10.0 ± 4.6 | 18.4 ± 3.9* | 17.4 ± 4.0* | 16.8 ± 4.1* | 15.9 ± 3.5* | 15.9 ± 4.2* | 16.7 ± 3.4* | 17.8 ± 3.9* |
| Control | 9.0 ± 3.0 | 18.6 ± 4.6* | 19.0 ± 5.7* | 17.7 ± 3.3* | 17.9 ± 4.1* | 18.3 ± 4.0* | 17.6 ± 4.6* | 18.3 ± 5.1* |
| VD/VT | | | | | | | | |
| Computer | 52.1 ± 10.2 | 70.5 ± 5.8* | 68.0 ± 5.2 | 66.0 ± 5.0* | 67.5 ± 6.1* | 67.3 ± 5.2* | 71.6 ± 5.3* | 69.6 ± 4.1* |
| Control | 45.6 ± 12.1 | 63.3 ± 8.5* | 68.3 ± 6.0* | 67.9 ± 7.4* | 67.5 ± 7.2* | 65.6 ± 8.1* | 64.4 ± 10* | 66.9 ± 4.6* |

Mean ± S.D.
*P < 0.05 within Groups
+P < 0.05 between Groups
Bonferroni's correction applied for multiple comparisons
Computer Group n = 7
Control Group n = 6
$PeCO_2$ = end expired $CO_2$
QS/QT = shunt fraction
VD/VT = dead space ventilation

TABLE 7

| Variable | Hypothermia | Rewarming |
|---|---|---|
| Temp °C. | | |

TABLE 7-continued

| Variable | Hypothermia | Rewarming |
|---|---|---|
| Computer | 28.4 ± .3 | 35.6 ± .82* |
| Control | 28.0 ± .24 | 35.0 ± .91* |
| MAP (mm Hg) | | |
| Computer | 91 ± 26 | 93 ± 17 |
| Control | 81 ± 13 | 82 ± 10+ |
| CSFP (mm Hg) | | |
| Computer | 9.1 ± 3 | 14.6 ± 3.7* |
| Control | 8.2 ± 4.3 | 12.3 ± 4.1*+ |
| CPP (mm Hg) | | |
| Computer | 82 ± 26 | 80 ± 19 |
| Control | 72 ± 15 | 69 ± 11 |

Computer n = 6
Control n = 6
*p < 0.05 within groups
+ p < 0.05 between groups

TABLE 8

| Variable | Hypothermia | Rewarming |
|---|---|---|
| Hgb (g/dl) | | |
| Computer | 7.4 ± .7 | 8.1 ± .9 |
| Control | 7.7 ± 1.1 | 7.7 ± 1 |
| $PaCO_2$ (mm Hg) | | |
| Computer | 37 ± 2 | 36 ± 1 |
| Control | 38 ± 2 | 36 ± 6 |
| pH | | |
| Computer | 7.35 ± .01 | 7.35 ± .02 |
| Control | 7.33 ± .02 | 7.35 ± .08 |
| Cont Diff (Vol %) | | |
| Computer | 4.4 ± 1.2 | 4.3 ± 1.1 |
| Control | 3.6 ± 0.7 | 4.9 ± 1.1* |
| SSS $PO_2$ (mm Hg) | | |
| Computer | 44 ± 6 | 42 ± 7* |
| Control | 44 ± 3 | 38 ± 4*+ |
| SSS Sat (%) | | |
| Computer | 68 ± 11 | 67 ± 10 |
| Control | 69 ± 6 | 60 ± 7*+ |

Computer n = 6
Control n = 6
*p < 0.05 within groups
+ p < 0.05 between groups

TABLE 9

| Variable | Hypothermia | Rewarming |
|---|---|---|
| tCBF (ml.g$^{-1}$.min$^{-1}$) | | |
| Computer | .18 ± .08 | .36 ± .07* |
| Control | .17 ± .06 | .33 ± .06* |
| hCBF (ml.g$^{-1}$.min$^{-1}$) | | |
| Computer | .17 ± .1 | .35 ± .08* |
| Control | .17 ± .06 | .32 ± .06* |
| bsCBF (ml.g$^{-1}$.min$^{-1}$) | | |

TABLE 9-continued

| Variable | Hypothermia | Rewarming |
|---|---|---|
| Computer | .21 ± .11 | .41 ± .07* |
| Control | .20 ± .07 | .38 ± .08* |
| FLOW:METABOLISM | | |
| Computer | 23.1 ± 5.2 | 23.9 ± 5.0 |
| Control | 28.6 ± 5.6 | 22.3 ± 4.3* |
| $CMRO_2$ | | |
| Computer | .008 ± .004 | .016 ± .008* |
| Control | .006 ± .002 | .014 ± .002* |

Computer n = 6
Control n = 6
*p < 0.005 within groups
+ p < 0.005 between groups

What we claim is:

1. Apparatus for controlling the flow of a biological fluid to an organ, which comprises:

means for establishing a pattern of variations over time of instantaneous changes in flow of a biological fluid to an organ of a mammalian species, means for generating a variable control parameter for regulation of flow of the biological fluid to an organ in accordance with the pattern, and means for controlling the flow of the biological fluid to the organ in accordance with the variable control parameter.

2. An apparatus for controlling the flow of blood by a pump to a body during cardiopulmonary by-pass, which comprises:

means for establishing a predetermined pattern of variation over time of instantaneous blood pressure and heart rate of an independently-functioning heart of a mammalian species;

means for generating a signal corresponding in value to an individually-determined blood pressure for a period of time corresponding to the heart rate for a difference between such individually-determined blood pressure and the next individually-determined blood pressure of said predetermined pattern;

means for generating a control voltage corresponding in magnitude to said signal; and means for applying said control voltage to said pump to provide an output of blood from said pump to the body during cardiopulmonary bypass of a pressure proportional to the magnitude of the signal for said period of time; and means for repeating the steps of generating a signal, generating a control voltage and applying the control voltage to the pump for each next individually-determined blood pressure of said predetermined pattern.

* * * * *